(12) United States Patent
Yamaue

(10) Patent No.: US 8,703,713 B2
(45) Date of Patent: Apr. 22, 2014

(54) COMBINATION THERAPY FOR PANCREATIC CANCER USING AN ANTIGENIC PEPTIDE AND CHEMOTHERAPEUTIC AGENT

(75) Inventor: Hiroki Yamaue, Wakayama (JP)

(73) Assignee: Onco Therapy Science, Inc., Kanagawa (JP)

( * ) Notice: Subject to any disclaimer, the term of this patent is extended or adjusted under 35 U.S.C. 154(b) by 373 days.

(21) Appl. No.: 12/674,754

(22) PCT Filed: Aug. 19, 2008

(86) PCT No.: PCT/JP2008/002232
§ 371 (c)(1),
(2), (4) Date: Dec. 6, 2010

(87) PCT Pub. No.: WO2009/028150
PCT Pub. Date: Mar. 5, 2009

(65) Prior Publication Data
US 2011/0082088 A1 Apr. 7, 2011

Related U.S. Application Data

(60) Provisional application No. 60/957,923, filed on Aug. 24, 2007.

(51) Int. Cl.
*A61K 38/00* (2006.01)
(52) U.S. Cl.
USPC ....................................................... 514/19.3
(58) Field of Classification Search
None
See application file for complete search history.

(56) References Cited

U.S. PATENT DOCUMENTS

| | | | |
|---|---|---|---|
| 3,265,572 A | 8/1966 | Moses | |
| 4,808,614 A | 2/1989 | Hertel | |
| 5,712,380 A | 1/1998 | Kendall et al. | |
| 6,348,333 B1 | 2/2002 | Niwa et al. | |
| 7,422,741 B2 * | 9/2008 | Alitalo et al. | 424/134.1 |
| 7,514,084 B2 | 4/2009 | Tahara et al. | |
| 7,556,809 B2 * | 7/2009 | Romero et al. | 424/185.1 |
| 7,695,720 B2 * | 4/2010 | Tahara et al. | 424/185.1 |
| 2005/0272688 A1 * | 12/2005 | Higgins et al. | 514/49 |
| 2006/0216288 A1 | 9/2006 | Chang | |
| 2006/0216301 A1 | 9/2006 | Tahara et al. | |
| 2010/0215676 A1 | 8/2010 | Tahara et al. | |
| 2012/0328636 A1 | 12/2012 | Tahara et al. | |
| 2013/0028923 A1 | 1/2013 | Tahara et al. | |

FOREIGN PATENT DOCUMENTS

| | | |
|---|---|---|
| CN | 1694901 A | 11/2005 |
| EP | 0921193 A1 | 6/1999 |
| EP | 1086705 A1 | 3/2001 |
| EP | 2119447 A1 | 11/2009 |
| GB | 213645 A | 3/1924 |
| JP | 2007/191485 A | 8/2007 |
| JP | 2008/524218 A | 7/2008 |
| RU | 2376373 C2 | 12/2009 |
| WO | WO 94/21679 A1 | 9/1994 |
| WO | WO 98/11223 A1 | 3/1998 |
| WO | WO 98/31794 A1 | 7/1998 |
| WO | WO 99/40118 A1 | 8/1999 |
| WO | WO 99/43801 A1 | 9/1999 |
| WO | WO 99/59636 A1 | 11/1999 |
| WO | WO 02/056907 A2 | 7/2002 |
| WO | 03/086450 * | 10/2003 |
| WO | 2004024766 * | 3/2004 |
| WO | WO 2004/024766 A1 | 3/2004 |
| WO | 2004/041203 A2 | 5/2004 |
| WO | 2005/000895 A2 | 1/2005 |
| WO | 2006/065525 A | 6/2006 |
| WO | WO 2008/099908 A1 | 8/2008 |

OTHER PUBLICATIONS

Johnson et al Cancer Treatment Reviews vol. 2 p. 1 (1975).*
Burgess et al, Journal of Cell Biology vol. 111 Nov. 1990 2129-2138).*
Lazar et al Molecular and Cellular Biology Mar. 1988 vol. 8 No. 3 1247-1252.*
Bicknell, R., et al., "Mechanisms and therapeutic implications of angiogenesis," *Curr. Opin. Oncol.*, vol. 8(1), pp. 60-65 (Jan. 1996).
Binetruy-Tournaire, R. et al., "Identification of a peptide blocking vascular endothelial growth factor (VEGF)-mediated angiogenesis," *EMBO*, vol. 19(7), pp. 1525-1533 (Apr. 3, 2000).
Bruns, C., et al., "Effect of the vascular endothelial growth factor receptor-2 antibody DC101 plus gemcitabine on growth, metastasis and angiogenesis of human pancreatic cancer growing orthotopically in nude mice," *Int. J. Cancer*, Vo. 102(2), pp. 101-108 (Nov. 10, 2002).
Flamme, I., et al., "Vascular Endothelial Growth Factor (VEGF) and VEGF Receptor 2 (flk-1) are Expressed during Vasculogenesis and Vascular Differentiation in the Quail Embryo," *Dev. Biol.*, vol. 169(2), pp. 699-712 (Jun. 1995).
Folkman, J., "Angiogenesis in cancer, vascular, rheumatoid and other disease," *Nat. Med.*, vol. 1(1), pp. 27-31 (Jan. 1995).
Greenlee, R., et al., "Cancer Statistics, 2001," *CA Cancer J. Clin.*, vol. 51(1), pp. 15-36 (Jan.-Feb. 2001).
Hou, J-M., et al., "Combination of Low-Dose Gemcitabine and Recombinant Quail Vascular Endothelial Growth Factor Receptor-2 as a Vaccine Induces Synergistic Antitumor Activities," *Oncology*, vol. 69(1), pp. 81-87 (2005, Epub Aug. 2, 2005).
Huang, et al., Combined Therapy of Local and Metastatic 4T1 Breast Tumor in Mice Using SU6668, an Inhibitor of Angiogenic Receptor Tyrosine Kinases, and the Immunostimulator B7.2-IgG Fusion Protein, *Cancer Res.*, vol. 62(20), pp. 5727-5735 (Oct. 15, 2002).
Ishizaki, H., et al., "Inhibition of Tumor Growth with Antiangiogenic Cancer Vaccine Using Epitope Peptides Derived from Human Vascular Endothelial Growth Factor Receptor 1," *Clin. Cancer Res.*, vol. 12(19), pp. 5841-5849 (Oct. 1, 2006).
Kindler, H., et al., "Phase II Trial of Bevacizumab Plus Gemcitabine in Patients with Advanced Pancreatic Cancer," *J. Clin. Oncol.*, vol. 23(31), pp. 8033-8040 (Nov. 1, 2005).

(Continued)

Primary Examiner — Sheela J Huff
(74) Attorney, Agent, or Firm — Kilpatrick Townsend & Stockton LLP

(57) ABSTRACT

Described herein is a combination therapy suited to the treatment of pancreatic cancer and the like. Also described is a method of potentiating the therapeutic effect of chemotherapeutic agents such as gemcitabine.

4 Claims, 7 Drawing Sheets

(56) References Cited

OTHER PUBLICATIONS

Klinkenbijl, J., et al., "Adjuvant Radiotherapy and 5-Fluorouracil After Curative Resection of Cancer of the Pancreas and Periampullary Region," *Ann. Surg.*, vol. 230(6), pp. 776-782, discussion 782-784 (Dec. 1999).
Kondo, A., et al., "Prominent Roles of Secondary Anchor Residues in Peptide Binding to HLA-A24 Human Class I Molecules," *J. Immunol.*, vol. 155(9), pp. 4307-4312 (Nov. 1, 1995).
Krause, S., et al., "Vascular Endothelial Growth Factor Antisense Pretreatment of Bladder Cancer Cells Significantly Enhances the Cytotoxicity of Mitomycin C, Gemcitabine and Cisplatin," *J. Urol.*, vol. 174(1), pp. 328-331 (Jul. 2005).
Kubo, R., et al., "Definition of Specific Peptide Motifs for Four Major HLA-A Alleles," *J. Immunol.*, vol. 152(8), pp. 3913-3924 (Apr. 15, 1994).
Li, Y., et al., "Active Immunization Against the Vascular Endothelial Growth Factor Receptor flk1 Inhibits Tumor Angiogenesis and Metastasis," *J. Exp. Med.*, vol. 195(12), pp. 1575-1584 (Jun. 17, 2002).
Liu, J-Y., et al., "Immunotherapy of tumors with vaccine based on quail homologous vascular endothelial growth factor receptor-2," *Blood*, vol. 102(5), pp. 1815-1823 (Sep. 1, 2003; Epub May 15, 2003).
Miyazawa, M., et al., "The combination therapy of an epitope peptide molecularly targeting VEGFR2 and gemcitabine for pancreatic cancer," *Suizo*, vol. 23(3), p. 267, Abstract #S1-10, The $39^{th}$ Annual Meeting of the Japan Pacreas Society Jul. 30-31, 2008.
Mochimaru, H., et al., "Suppression of Choroidal Neovascularization by Dendritic Cell Vaccination Targeting VEGFR2," *Invest. Ophthalmol. Vis. Sci.*, vol. 48(10), pp. 4795-4801 (Oct. 2007).
Molina, M., et al., "Trastuzumab (Herceptin), a Humanized Anti-HER2 Receptor Monoclonal Antibody, Inhibits Basal and Activated HER2 Ectodomain Cleavage in Breast Cancer Cells," *Cancer Res.*, vol. 61(12), pp. 4744-4749 (Jun. 15, 2001).
Norgren, R., et al., EMBL Accession No. Q8SPP2 (Jun. 1, 2002).
Shinkai, et al., "Mapping of the Sites Involved in Ligand Association and Dissociation at the Extracellular Domain of the Kinase Insert Domain-containing Receptor for Vascular Endothelial Growth Factor," *J. Biol. Chem.*, vol. 273(47), pp. 31283-31288 (Nov. 20, 1998).
Sun, J. et al., "Both farnesyltransferase and geranylgeranyltransferase I inhibitors are required for inhibition of oncogenic K-Ras prenylation but each alone is sufficient to suppress human tumor growth in nude mouse xenografts," *Oncogene*, vol. 16(11), pp. 1467-1473 (Mar. 1998).
Tanaka, H., et al., "Immunogenicity and Specificity of HLA-A2.1-Restricted Peptides from Carcinoembryonic Antigen (CEA) and Nonspecific Cross-Redacting Antigen (NCA) in Transgenic Mice," *American Association for Cancer Research*, vol. 42, p. 681, Abstract #3669 (2001).
Wada, S., et al., "Development of cancer immunotherapy against tumor angiogenesis," *Proceedings of the American Association for Cancer Research*, vol. 44, $2^{nd}$ ed., p. 167, Abstract #848 (Jul. 2003).
Wada, S. et al., "Mechanism for cancer immunotherapy with peptide vaccination targeting tumor-angiogenesis," *Proceedings of the $64^{th}$ Annual Meeting of the Japanese Cancer Association*, p. 326, Abstract #W-471 (Aug. 15, 2005).
Wada, et al., "Development of a new type of cancer immunotherapy that targets tumor angiogenesis," *Jpn. J. Gastroenterol. Surg.*, vol. 58, p. 564, Abstract #PP-2-606 (2003).
Wada, et al., "Development of a cancer vaccine therapy that targets tumor angiogenesis," *J. Jpn. Surg. Soc.*, vol. 103, p. 533, Abstract PS3124-3 (2003).
Wada, S., et al., "Development of the new cancer vaccine treatment that can be opposed to escape mechanism of immunological,"*Cancer Science* (*The $63^{rd}$ Annual Meeting of the Japanese Cancer Association*), vol. 95, Supplement, p. 436, Abstract W-464 (Aug. 25, 2004).
Wada, S., et al., "Development of cancer vaccine targeting tumor angiogenesis," *Cancer Science* (*The $62^{nd}$ Annual Meeting of the Japanese Cancer Association*), p. 202, Abstract #2267-OP (Aug. 25, 2003).
Wada, S., et al., "Rationale for Antiangiogenic Cancer Therapy with Vaccination Using Epitope Peptides Derived from Human Vascular Endothelial Growth Factor Receptor 2," *Cancer Res.*, vol. 65(11), pp. 4939-4946 (Jun. 1, 2005).
Waltenberger, J., et al., "Different Signal Transduction Properties of KDR and Flt1, Two Receptors for Vascular Endothelial Growth Factor," *J. Biol. Chem.*, vol. 269(43), pp. 26988-26995 (Oct. 28, 1994).
Yamaue, H., et al., "Phase I clinical trial with VEGFR2-epitope peptides and gemcitabine for patients with advanced pancreatic cancer," *Proceedings of the $66^{th}$ Annual Meeting of the Japanese Cancer Association*, pp. 256-257, Abstract SST5-5 (2007).
Zaremba, S., et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Falk, et al., "Allele-specific motifs revealed by sequencing of self-peptide eluted from MHC molecules," *Nature*, vol. 351(6324), pp. 290-296 (May 23, 1991).
Hoffman, et al., "The Ability of Variant Peptides to Reverse the Nonresponsiveness of T Lymphocytes to the Wild-Type Sequence $p53_{264-272}$ Epitope," *J Immunol.*, vol. 168(3), pp. 1338-1347 (Feb. 1, 2002).
Rammensee, et al., "MHC ligands and peptide motifs: first listing," *Immunogenetics*, vol. 41(4), pp. 178-228 (1995).
U.S. Appl. No. 13/494,930, 76 pages, filed Jun. 12, 2012.
U.S. Appl. No. 13/494,933, 76 pages, filed Jun. 12, 2012.
U.S. Appl. No. 13/377,110, which is a U.S. National Stage of PCT/JP2010/003871, filed Jun. 10, 2010, 69 pages.
Correale, P., et al., "Dendritic Cell-Mediated Cross-Presentation of Antigens Derived from Colon Carcinoma Cells Exposed to a Highly Cytotoxic Multidrug Regimen with Gemcitabine, Oxaliplatin, 5-Fluorouracil, and Leucovorin, Elicits a Powerful Human Antigen-Specific CTL Response with Antitumor Activity in Vitro," *J. Immunol.*, vol. 175(2), pp. 820-828 (Jul. 15, 2005).
Dauer, M., et al., "Chemosensitization of Pancreatic Carcinoma Cells to Enhance T Cell-Mediated Cytotoxicity Induced by Tumor Lysate-Pulsed Dendritic Cells," *J. Immunother.*, vol. 28(4), pp. 332-342 (Jul.-Aug. 2005).
Adams, et al., "Prediction of binding to MHC class I molecules," *J Immunol Methods*, vol. 185(2), pp. 181-190 (Sep. 25, 1995).
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).
2013 Gastrointestinal Cancers Symposium, Jan. 24-26, 2013.
Abstract from 2013 Gastrointestinal Cancers Symposium, http://gicasym.asco.org/content/105112-133, 5 pages (2013).

\* cited by examiner

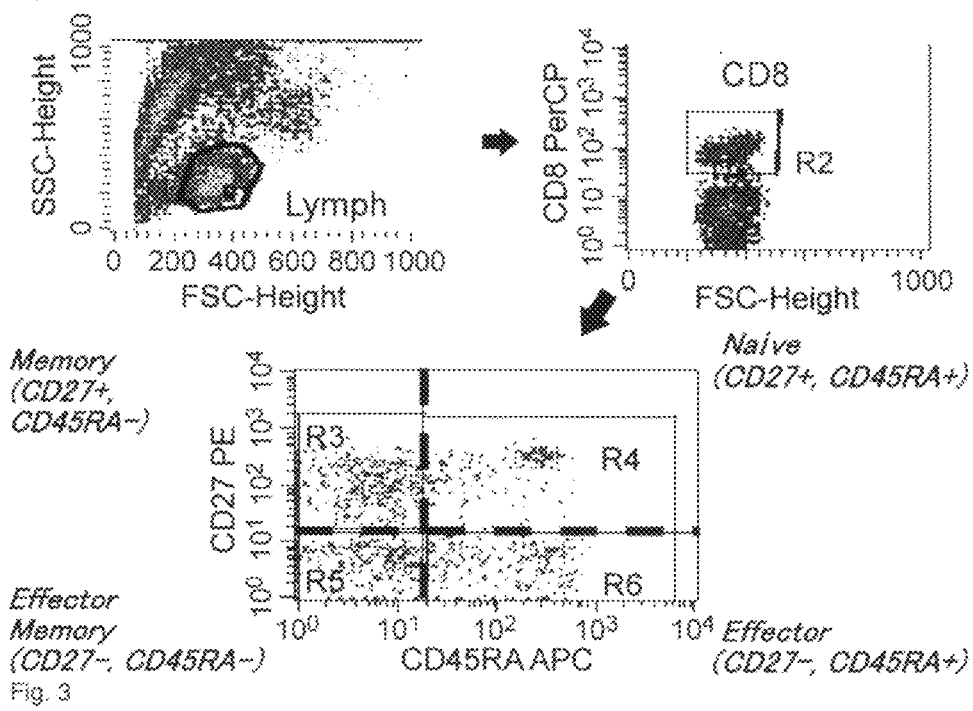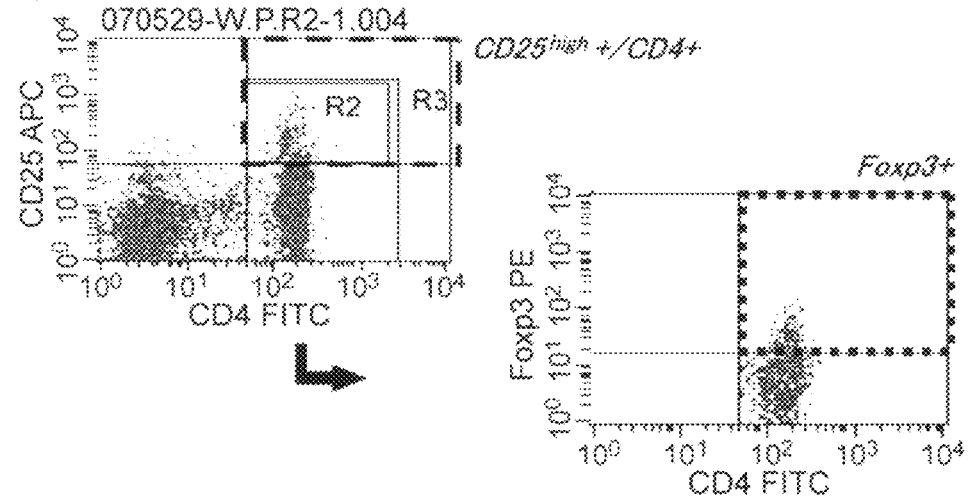

EVALUATION: SD

BEFORE PERFORMING VACCINATION (2007.05.02)

AFTER 1 COURSE (2007.07.03)

US 8,703,713 B2

COMBINATION THERAPY FOR PANCREATIC CANCER USING AN ANTIGENIC PEPTIDE AND CHEMOTHERAPEUTIC AGENT

PRIORITY

This application is a U.S. National Stage Application of PCT/JP2008/002232, filed Aug. 19, 2008, which claims the benefit of U.S. Provisional Application Ser. No. 60/957,923 filed Aug. 24, 2007, the contents of which are hereby incorporated by reference in their entirety.

TECHNICAL FIELD

The present invention relates to a novel combination therapy for pancreatic cancer that utilizes an antigenic peptide and chemotherapeutic agent.

BACKGROUND ART

Pancreatic cancer has one of the highest mortality rates of any malignancy, and the 5-year-survival rate of patients is 4%. Approximately 28,000 patients are diagnosed with pancreatic cancer each year, and nearly all patients will die of their disease (Greenlee, R. T., et al., (2001) CA Cancer J Clin, 51: 15-36). The poor prognosis of this malignancy results from the difficulty of early diagnosis and the poor response to current therapeutic methods (Greenlee, R. T., et al. (2001) CA Cancer J Clin, 51: 15-36, Klinkenbijl, J. H., et al. (1999) Ann Surg, 230: 776-82; discussion 782-4.). In particular, there are currently no identified tumor markers that allow for reliable screening at an early, potentially curative stage of the disease.

Research aimed at the elucidation of carcinogenic mechanisms has revealed a number of candidate target molecules for the development of anti-tumor agents. For example, the farnesyltransferase inhibitor (FTI) has been shown to be effective in the treatment of Ras-dependent tumors in animal models (Sun J et al., (1998) Oncogene, 16:1467-73.). This pharmaceutical agent was subsequently developed to inhibit growth signal pathways related to Ras, which is dependant on post-transcriptional farnesylation. Human clinical trials in which anti-tumor agents were applied in combination with the anti-HER2 monoclonal antibody, trastuzumab, in order to antagonize the proto-oncogene HER2/neu have succeeded in improving clinical response, and improved the overall survival rate of breast cancer patients. Tyrosine kinase inhibitor STI-571 is an inhibitor which selectively deactivates the bcr-abl fusion protein. This pharmaceutical agent was subsequently developed for the therapy of chronic myeloid leukemia, wherein the constant activation of bcr-abl tyrosine kinase plays a significant role in the transformation of white blood cells. Such pharmaceutical agents are designed to inhibit the carcinogenic activity of specific gene products (Molina M A, et al., (2000) Cancer Res, 16:4744-9). Thus, in cancer cells, gene products with promoted expression generally serve as potential targets for the development of novel anti-tumor agents. Alternatively, nucleic acid synthesis inhibitors may also be used as anti-tumor agents. For example, gemcitabine (Gemzar$^R$) is a first-line treatment of pancreatic cancer. The combination therapy of gemcitabine and paclitaxel has also been applied to treatment of pancreatic cancer.

Meanwhile, tumor angiogenesis is critically involved in the progression of tumors. It has previously been demonstrated that an effective vaccine against tumor angiogenesis could be developed according to an endothelial cell-based approach, targeting vascular endothelial growth factor receptors (VEGFRs) 1 and 2, as HLA class I molecules are not down-regulated on endothelial cells (Wada S et al., Cancer Res 2005 Jun. 1, 65(11): 4939-46; Ishizaki H et al., Clin Cancer Res 2006 Oct. 1, 12(19): 5841-9). Peptides that induce cytotoxic T lymphocytes (CTLs) specific to cells expressing VEGFR and thereby suppress tumor angiogenesis with a specific and efficient CTL response have been previously described as well (See WO/2004/024766, incorporated by reference herein).

The present invention addresses the need in the art for an improved pancreatic cancer therapy by providing a novel combination therapy for pancreatic cancer that utilizes an antigenic peptide, particularly antigenic peptides and cancer vaccines that target VEGFR2, and a chemotherapeutic agent such as gemcitabine.

DISCLOSURE OF INVENTION

Summary of the Invention

In view of the state of the art of cancer therapy, it was an object of the present invention to find a means to enhance the therapeutic effect of chemotherapy. VEGFR2 is strongly expressed in tumoral tissue endothelial cells and is thought be involved in the proliferation of endothelial cells on the VEGF signal. Accordingly, the present invention focused on possible cancer vaccine therapies that target VEGFR2 (KDR/flk-1; referred to below as KDR). It was subsequently discovered that the therapeutic effect of chemotherapeutic agents such as gemcitabine is potentiated by VEGFR2 (KDR/flk-1; referred to below as KDR) peptides that induce cytotoxic T-cells against cells expressing VEGFR2. Thus, it is an object of the present invention to provide:

[1]. A method of treating cancer in a subject that includes the step of administering to the subject (i) and (ii);
  (i) one or more peptides selected from the group consisting of;
    (a) one or more peptides having the amino acid sequence selected from the group consisting of RFVPDGNRI (SEQ ID NO: 1), VYSSEEAEL (SEQ ID NO: 2), GYRIYDVVL (SEQ ID NO: 3), SYMISYAGM (SEQ ID NO: 4), KWEFPRDRL (SEQ ID NO: 5), DFLTLEHLI (SEQ ID NO: 6),
    (b) the peptide of (a), wherein 1, 2, or several amino acids are substituted, deleted, or added, and wherein said peptide having cytotoxic T cell inducibility;
    (c) the peptide of (b), wherein the second amino acid from the N-terminus is phenylalanine, tyrosine, methionine, or tryptophan;
    (d) the peptide of (b) or (c), wherein the C-terminal amino acid is phenylalanine, leucine, isoleucine, tryptophan, or methionine;
    (e) one or more peptides having the amino acid sequence selected from the group consisting of AMFFWLLLV (SEQ ID NO: 7), VIAMFFWLL (SEQ ID NO: 8), AVIAMFFWL (SEQ ID NO: 9), KLIEIGVQT (SEQ ID NO: 10), YMISYAGMV (SEQ ID NO: 11), IQSDVWSFGV (SEQ ID NO: 12), and VLAMFFWLL (SEQ ID NO: 13);
    (f) the peptide of (e), wherein 1, 2, or several amino acids are substituted, deleted, or added, and wherein said peptide having cytotoxic T cell inducibility;
    (g) the peptide of (f), wherein the second amino acid from the N-terminus is leucine or methionine; and
    (h) the peptide of (f) or (g), wherein the C-terminal amino acid is valine or leucine.
  (ii) one or more chemotherapeutic agents selected from the group consisting of gemcitabine, a pharmaceutically acceptable salt thereof, and a prodrug thereof.

[2]. The method of [1], wherein the subject is HLA-A24-positive or HLA-A02-positive.

[3]. The method of [1], wherein the cancer is pancreatic cancer.

[4]. A kit for treating cancer in a subject containing pharmaceutical compositions that include (i) and (ii) as active ingredient respectively and pharmaceutical acceptable carrier;

(i) one or more peptides selected from the group consisting of (a)-(h) of [1]-(i); and (ii) one or more chemotherapeutic agents selected from the group consisting of gemcitabine, a pharmaceutically acceptable salt thereof, and a prodrug thereof.

[5]. The kit of [4], wherein the subject is HLA-A24-positive or HLA-A02-positive.

[6]. The kit of [4], wherein the cancer is pancreatic cancer.

[7]. An anti-cancer agent for treating cancer in a subject that includes (i) in combination with (ii);

(i) one or more peptides selected from the group consisting of (a)-(h) of [1]-(i); and (ii) one or more chemotherapeutic agents selected from the group consisting of gemcitabine, a pharmaceutically acceptable salt thereof, and a prodrug thereof.

[8]. The anti-cancer agent of [7], wherein the subject is HLA-A24-positive or HLA-A02-positive.

[9]. The anti-cancer agent of [7], wherein the cancer is pancreatic cancer.

[10]. Use of an combination of (i) and (ii) in the treatment of cancer in a subject;

(i) one or more peptides selected from the group consisting of (a)-(h) of [1]-(i); and (ii) one or more chemotherapeutic agents selected from the group consisting of gemcitabine, a pharmaceutically acceptable salt thereof, and a prodrug thereof.

[11]. The use of [10], wherein the subject is HLA-A24-positive or HLA-A02-positive.

[12]. The use of [10], wherein the cancer is pancreatic cancer.

[13]. Use of one or more peptides selected from the group consisting of (a)-(h) of [1]-(i) for manufacturing a pharmaceutical composition that enhances the therapeutic effect of gemcitabine.

[14]. The use of [13], wherein the therapeutic effect to be enhanced is a therapeutic effect of gemcitabine on the treatment of a cancer in a subject, wherein the subject is HLA-A24-positive or HLA-A02-positive.

[15]. The use of [14], wherein the cancer is pancreatic cancer.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows:

FIG. 1 presents the administration protocol for the antigenic peptide and chemotherapeutic agent utilized in the present examples.

FIG. 2 presents the results of flow cytometry analysis of naive, memory, and effector T cells among CD8-positive T cells, wherein the functional lymphocyte fractions were determined by perforin staining.

FIG. 3 presents the numerical change of regulatory T cells (e.g., CD25high and Foxp3-positive cells among CD4-positive T cells) before and after vaccine administration as measured by flow cytometry after four color staining.

DETAILED DESCRIPTION OF THE INVENTION

Figure 4:
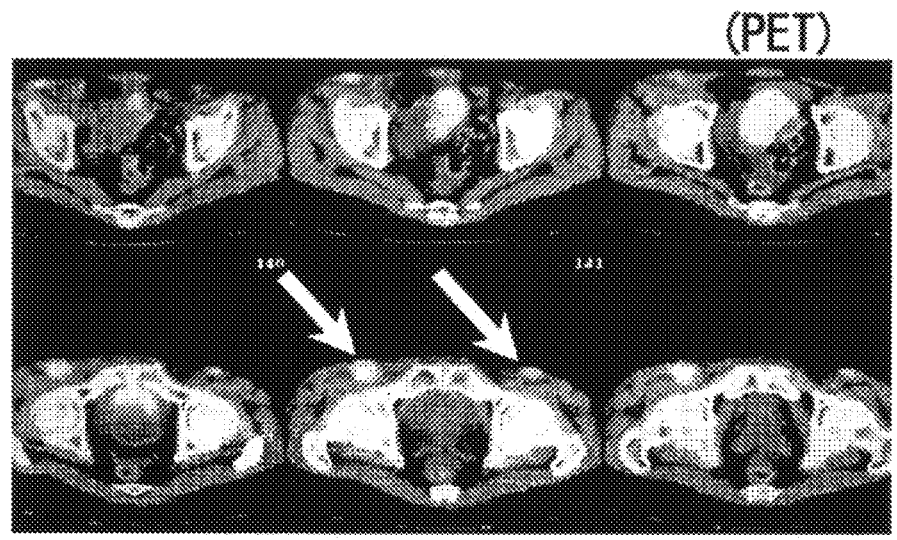
FIG. 4 presents the results of a PET scan on Case 3, particularly a lymphadenopathy near the inoculation site after vaccination.

Although methods and materials similar or equivalent to those described herein can be used in the practice or testing of embodiments of the present invention, the preferred methods and materials are now described. However, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

DEFINITIONS

The words "a", "an", and "the" as used herein mean "at least one" unless otherwise specifically indicated.

In the context of the present invention, the term "several" as applies to amino acid additions, deletions, and/or substitutions means 3-7, preferably 3-5, more preferably 3-4, even more preferably 3 amino acid residues.

As used herein, the term "organism" refers to any living entity composed of at least one cell. A living organism can be as simple as, for example, a single eukaryotic cell or as complex as a mammal, including a human being.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). The term "biological sample" further refers to a homogenate, lysate, extract, cell culture or tissue culture prepared from a whole organism or a subset of its cells, tissues or component parts, or a fraction or portion thereof. Lastly, "biological sample" refers to a medium, such as a nutrient broth or gel in which an organism has been propagated, which contains cellular components, such as proteins or polynucleotides.

The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The terms "polynucleotides", "oligonucleotides" "nucleotides", "nucleic acids", and "nucleic acid molecules" are used interchangeably herein to refer to a polymer of nucleic acid residues and, unless otherwise specifically indicated, are similarly to the amino acids referred to by their commonly accepted single-letter codes. Similar to the amino acids, they encompass both naturally-occurring and non-naturally occurring nucleic acid polymers.

The term "chemotherapeutic agent" as used herein refers to a chemical compound useful in the treatment of cancer. Examples of chemotherapeutic agents include, but are not limited to, the following and their pharmaceutically acceptable salts, acids and derivatives: alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembiehin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, poffiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofrran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and doxetaxel (TAXOTEW, Rhóne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine; Also included in this definition are anti-hormonal agents that act to regulate or inhibit hormone action on tumors such as anti-estrogens including for example tamoxifen, raloxifene, aromatase inhibiting 4 (5)-imidazoles, 4 hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

Antigenic Peptides:

As noted above, the present invention relates to agents that enhance or improve the therapeutic effect of chemotherapy, more particularly antigenic peptides that target VEGFR2, induce cytotoxic T-cells against cells expressing VEGFR2, and subsequently enhance or improve the therapeutic effect of chemotherapeutic agents such as gemcitabine.

Antigenic peptides having subsequences of VEGFR2 may be used for the method, kit, or composition of the present invention. Antigenic peptides suitable for use in the context of the present invention preferably have an amino acid sequence selected from those shown bellow.

| | |
|---|---|
| VYSSEEAEL, | (SEQ ID NO: 2) |
| GYRIYDVVL, | (SEQ ID NO: 3) |
| SYMISYAGM, | (SEQ ID NO: 4) |
| RFVPDGNRI, | (SEQ ID NO: 1) |
| KWEFPRDRL, or | (SEQ ID NO: 5) |
| DFLTLEHLI. | (SEQ ID NO: 6) |

Mutated or modified peptides, peptides having amino acid sequences modified by deleting, adding and/or replacing one or more amino acid residues of a certain amino acid sequence, have been known to retain the original biological activity (Mark, D. F. et al., Proc. Natl. Acad. Sci. USA (1984) 81, 5662-5666, Zoller, M. J. and Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413). Accordingly, the present invention contemplates variations and modifications to the above sequences. In particular, antigenic peptides in which one, two, or several amino acids are substituted with or added to one of the amino acid sequences mentioned above also find utility in the context of the present invention, provided the resulting modified peptides retain the requisite cytotoxic T cell inducibility. Such modified peptides, having CTL inducibility as well as an amino acid sequence as mentioned above, in which one, two, or several amino acids are substituted or added, are contemplated herein provided they do not match the amino acid sequence of another protein.

Accordingly, in one preferred embodiment, the second amino acid from the N terminus is preferably substituted to phenylalanine, tyrosine, methionine, or tryptophan, or the C-terminal amino acid is preferably substituted to phenylalanine, leucine, isoleucine, tryptophan, or methionine; or one or two amino acids are added to the N terminus and/or C terminus.

Alternatively, nonapeptides and decapeptides selected from peptides having the amino acid sequence shown below are also preferred as peptide having high CTL inducibility.

```
AMFFWLLLV,      (SEQ ID NO: 7)

VIAMFFWLL,      (SEQ ID NO: 8)

AVIAMFFWL,      (SEQ ID NO: 9)

KLIEIGVQT,      (SEQ ID NO: 10)

YMISYAGMV,      (SEQ ID NO: 11)

IQSDVWSFGV,     (SEQ ID NO: 12)
or

VLAMFFWLL.      (SEQ ID NO: 13)
```

In the context of the present invention, peptides with cytotoxic T cell inducibility, wherein one, two, or several amino acids are substituted or added to one of the amino acid sequence as mentioned above may also be used. Peptides having the amino acid sequences composed of nine or ten amino acids as mentioned above, in which one, two, or several amino acids are substituted or added, may have CTL inducibility so long as they do not match the amino acid sequence of another protein. In particular, for example, the second amino acid from the N terminus is preferably substituted to leucine or methionine, or the C-terminal amino acid is preferably substituted to valine or leucine; or one or two amino acids are added to the N terminus and/or C terminus.

An example of such a modified peptide is the peptide of VIAMFFWLL (SEQ ID NO: 8), in which the second amino acid from the N terminus is substituted to leucine (VLAMFFWLL (SEQ ID NO: 13)); however, the present invention is not limited to this example. CTL clones obtained from stimulation with these modified peptides can recognize the original peptides, and cause damage.

Examples of contemplated amino acid sequence insertions include amino- and/or carboxyl-terminal fusions ranging in length from one to several residues, as well as intrasequence insertions of single or multiple amino acid residues. Examples of terminal insertions include an N-terminal methionyl residue or the antibody fused to a cytotoxic polypeptide. The peptides used for the present invention may also contain modifications, such as glycosylation, side chain oxidation, or phosphorylation, so long as the modifications do not destroy the biological activity of the peptides as described herein. Other modifications include fusions of an enzyme or a polypeptide which increases the serum half-life of the antibody to the N- or C-terminus of the peptide. Examples of the latter include D-amino acids or other amino acid mimetics.

In the context of amino acid insertions, wherein one or more amino acids residues are added to a peptide of the present invention, the present invention also contemplates fusion proteins. Fusion proteins are generally composed of a polypeptide or protein of interest with a polypeptide or protein of known utility. Fusion proteins can be made by techniques well known to a person skilled in the art, such as by linking a DNA encoding a peptide of the present invention with DNA encoding other peptides or proteins, so that the frames match, inserting the fusion DNA into an expression vector and expressing it in a host. There is no restriction as to the peptides or proteins fused to the protein of the present invention. However, examples of known peptides that can be used in the context of fusion proteins include, but are not limited to, FLAG (Hopp, T. P. et al., Biotechnology (1988) 6, 1204-1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, alpha-tubulin fragment, B-tag, Protein C fragment, and the like. Examples of proteins that may be fused to a protein of the invention include GST (glutathione-S-transferase), Influenza agglutinin (HA), immunoglobulin constant region, beta-galactosidase, MBP (maltose-binding protein), and such. In the context of amino acid substitutions, the amino acid residue to be substituted is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

Antigenic peptides of the present invention can be prepared using well known techniques. For example, the peptides can be prepared synthetically, using either recombinant DNA technology or chemical synthesis. Peptides may be synthesized individually or as longer polypeptides composed of two or more peptides. These peptides are preferably isolated, i.e., substantially free of other naturally occurring host cell proteins and fragments thereof.

The antigenic peptides of the present invention may be provided in a cocktail or may be conjugated to each other using standard techniques. For example, the peptides can be expressed as a single polypeptide sequence. The peptides in the combination may be the same or different. By administering the peptides of this invention, the peptides are presented at a high density on the HLA antigens of antigen-presenting cells, which, in turn, induces CTLs that specifically react toward the complex formed between the displayed peptide and the HLA antigen. Alternatively, antigen-presenting cells having immobilized the peptides of this invention on their cell surface, obtained by removing dendritic cells from the subjects, may be stimulated by the peptides of this invention. Re-administration of these cells to the respective subjects induces CTL, and, as a result, aggressiveness towards the target cells can be increased.

Pharmaceutical Compositions and Methods of Use Thereof:

The present invention provides drugs for treating and/or preventing pancreatic cancer used for in combination with a chemotherapeutic agent such as gemcitabine. The peptides used for the invention find particular utility in the treatment of pancreatic cancer.

In vivo and in vitro stimulation of dendritic cells by the antigenic peptides of the present invention can be easily performed by exposing the cells to a high concentration of the peptides, which causes these peptides to replace the peptides originally immobilized on the cells. Therefore, to be useful in the context of the present invention, the antigenic peptides must have at least a certain level of binding affinity to HLA antigens.

The pharmaceuticals containing such peptides may be directly administered as the peptides themselves, or may be administered as pharmaceutical compositions that have been formulated by conventional formulation methods. In such cases, the pharmaceuticals can appropriately include, in addition to the peptides, carriers, excipients, and such that are ordinarily used for pharmaceuticals, without particular limitations. The pharmaceuticals can be used for treatment and prevention of pancreatic cancer in combination with gemcitabine.

Pharmaceuticals for treating and/or preventing pancreatic cancer including an antigenic peptide of the present invention as an active ingredient, can be administered with adjuvants that effectively induce cellular immunity; can be administered with other active ingredients such as antitumor agents; and can be administered in granular forms. Suitable adjuvants are described in the literature (Clin. Microbiol. Rev., 7:277-289, 1994). Furthermore, the pharmaceuticals of this invention can be administered as liposome formulations, as granular formulations bound to beads of a few micrometers in diameter, and as formulations to which lipids are bound.

Administration methods may be carried out, for example, orally, intradermally, or subcutaneously, or through intravenous injection, or such. Systemic administration or local administration to the vicinity of the target tumor or directly into the target tumor may be applicable. Doses of the peptides of this invention can be adjusted appropriately, depending on the disease to be treated, age and weight of the patients, administration methods, and such. Ordinarily, 0.001 mg to 1,000 mg, preferably 0.001 mg to 1,000 mg, more preferably 0.1 mg to 10 mg, of the peptides are preferably administered once in a few days to a few months. More specifically, in order to enhance the therapeutic effect of gemcitabine, in a preferred embodiment, 0.5 mg to 2.0 mg of the peptides may be administered once in a few days to a few months, more preferably in a week (7 days), in combination with gemcitabine. One skilled in the art can appropriately select suitable doses.

Alternatively, in the context of the present invention, intracellular vesicles which present complexes formed between the peptides of this invention and HLA antigens on their surface may be used for the purpose of the present invention. These intracellular vesicles are called exosomes. Exosomes can be prepared, for example, according to the methods specifically described in Published Japanese Translation of International Publication Nos. Hei 11-510507 and 2000-512161. Exosomes can preferably be prepared using antigen-presenting cells obtained from subjects who are to be the target of therapy or prophylaxis. The exosomes of this invention can be inoculated as cancer vaccines, as for the peptides of this invention.

The type of HLA antigens to be used must match that of the subject in need of therapy and/or prophylaxis. For example, for Japanese people, HLA-A24 or HLA-A02, particularly HLA-A2402 or HLA-0201, is often appropriate.

Similarly, in the context of the present invention, isolated cytotoxic T cells, that are induced by the peptides may also be used for the purpose of the present invention. The cytotoxic T cells, which have been induced by stimulation with antigen-presenting cells that present the peptides of this invention, are preferably derived from subjects to be the target of therapy and/or prophylaxis. The cytotoxic T cells can be administered alone or, for the purpose of antitumor effect, in combination with other drugs, including the peptides, exosomes and so on of this invention. The obtained cytotoxic T cells act specifically against target cells presenting the peptides of this invention, or preferably, against target cells presenting the same peptides used for induction. The target cells may be cells that endogenously express KDR, or cells forced to express KDR. Furthermore, cells that present the peptides of this invention on their cell surface due to stimulation by these peptides can also be targeted.

In the context of the present invention, antigen-presenting cells that present complexes formed between HLA antigens and the peptides may also be used for the purpose of the present invention. The antigen-presenting cells that are obtained by contact with the peptides, or with nucleotides encoding the peptides, are preferably derived from subjects to be targeted for therapy and/or prophylaxis. The antigen-presenting cells can be administered as vaccines alone, or in combination with other drugs such as the peptides of this invention, exosomes, and cytotoxic T cells.

In the context of the present invention, the peptides are preferably administered in combination with gemcitabine. Gemcitabine is a common name given to the compound 2'-deoxy-2',2'-difluorocytidine monohydrochloride (b-isomer). A pharmaceutical composition composed of the hydrochloride salt of gemcitabine (gemcitabine HCl) is commonly commercially available as Gemzar (trade name). In the context of the present invention, at least one of gemcitabine, a pharmaceutically acceptable salt of gemcitabine, or a prodrug thereof may be administered in combination with the aforementioned peptides. Accordingly, unless otherwise stated, references herein to gemcitabine include its salt or prodrug.

Gemcitabine is a chemotherapeutic agent that is already in clinical use as a therapeutic agent for several cancers including pancreatic cancer. The standard therapeutic protocol for administering gemcitabine to an adult for the treatment of pancreatic cancer involves the administration of 1000 mg/m$^2$ of gemcitabine per week for up to seven weeks. Gemcitabine is typically administered by intravenous infusion. In pancreatic cancer therapy, generally, a schedule of three weeks of administration followed by one week of no treatment is set as one cycle, and the treatment is continued and repeated as needed. During this period, the dose of gemcitabine can be adjusted using hematologic toxicity or such as an indicator. In the present invention, the peptides are administered in accordance with such an administration schedule for gemcitabine. The antigenic peptides of the present invention can be administered at any stage during the gemcitabine administration period. Alternatively, so long as the CTLs that are induced by the antigenic peptides of the present invention maintain their activity in vivo, such peptides can be administered prior to gemcitabine administration. Generally, it is reasonable to administer them with the same schedule as for gemcitabine administration, thereby keeping the time commitment of the patient to a minimum.

As discovered herein, the administration of VEGFR2-derived peptides having amino acid sequences such as RFVPDGNRI (SEQ ID NO: 1) can improve the therapeutic effects of gemcitabine. The amino acid sequences of exemplary VEGFR2-derived peptides that can be used in the context of the present invention are described again below. In the context of the present invention, modified or mutated versions of these amino acid sequences can also be used in the present invention, so long as they retain the desired CTL-inducing ability.

| | |
|---|---|
| VYSSEEAEL, | (SEQ ID NO: 2) |
| GYRIYDVVL, | (SEQ ID NO: 3) |
| SYMISYAGM, | (SEQ ID NO: 4) |
| RFVPDGNRI, | (SEQ ID NO: 1) |
| KWEFPRDRL, | (SEQ ID NO: 5) |
| DFLTLEHLI, | (SEQ ID NO: 6) |
| AMFFWLLLV, | (SEQ ID NO: 7) |
| VIAMFFWLL, | (SEQ ID NO: 8) |
| AVIAMFFWL, | (SEQ ID NO: 9) |
| KLIEIGVQT, | (SEQ ID NO: 10) |
| YMISYAGMV, | (SEQ ID NO: 11) |
| IQSDVWSFGV, or | (SEQ ID NO: 12) |
| VLAMFFWLL. | (SEQ ID NO: 13) |

Therefore, the present invention provides agents that enhance the pancreatic cancer therapeutic effect of gemcitabine, such agents including the above-described VEGFR2-derived peptides as an active ingredient. Alternatively, the present invention provides uses of the VEGFR2-derived peptides in the production of pharmaceutical compositions that enhance the therapeutic effects of gemcitabine on pancreatic cancer. Furthermore, the present invention provides combined uses (combination) of the VEGFR2-derived peptides during pancreatic cancer therapy using gemcitabine.

According to the present invention, the VEGFR2-derived peptides can be used in combination with gemcitabine for pancreatic cancer therapy. More specifically, the present invention provides a kit for treating pancreatic cancer which is composed of a pharmaceutical composition that contains as active ingredients each of a pharmaceutically acceptable carrier, the aforementioned VEGFR2-derived peptides, and gemcitabine. Furthermore, the present invention provides anticancer agents for treating pancreatic cancer, which include a combination of the aforementioned VEGFR2-derived peptides and gemcitabine. Alternatively, the present invention provides a kit for treating pancreatic cancer which includes the aforementioned VEGFR2-derived peptides and an instruction sheet stating that the therapeutic effect of gemcitabine is enhanced when the peptides are administered in combination with gemcitabine to pancreatic cancer patients.

In another embodiment, the present invention also provides a use of a combination of the VEGFR2-derived peptides and one or more chemotherapeutic agents selected from the group consisting of gemcitabine, a pharmaceutically acceptable salt thereof, and a prodrug thereof, in manufacturing a pharmaceutical composition for treating a cancer including pancreatic cancer. Alternatively, in another embodiment, the present invention provides a use of the VEGFR2-derived peptides in manufacturing a pharmaceutical composition for treating a cancer including pancreatic cancer, wherein the pharmaceutical composition is used in combination with one or more chemotherapeutic agents selected from the group consisting of gemcitabine, a pharmaceutically acceptable salt thereof, and a prodrug thereof. In another embodiment, the present invention further provides a use of the VEGFR2-derived peptides in manufacturing a pharmaceutical composition for enhancing a therapeutic effect of one or more chemotherapeutic agents selected from the group consisting of gemcitabine, a pharmaceutically acceptable salt thereof, and a prodrug thereof, for treating a cancer including pancreatic cancer.

Alternatively, the present invention further provides a method or process for manufacturing a pharmaceutical composition for enhancing a therapeutic effect of one or more chemotherapeutic agents selected from the group consisting of gemcitabine, a pharmaceutically acceptable salt thereof, and a prodrug thereof, for treating a cancer including pancreatic cancer, wherein the method or process comprises the step of formulating a pharmaceutically or physiologically acceptable carrier with the VEGFR2-derived peptides as active ingredients. In another embodiment, the present invention further provides a method or process for manufacturing a pharmaceutical composition for enhancing a therapeutic effect of one or more chemotherapeutic agents selected from the group consisting of gemcitabine, a pharmaceutically acceptable salt thereof, and a prodrug thereof, for treating a cancer including pancreatic cancer, wherein the method or process comprises the step of admixing the VEGFR2-derived peptides with a pharmaceutically or physiologically acceptable carrier.

In another embodiment, the present invention also provides a method or process for manufacturing a kit for treating a cancer including pancreatic cancer, wherein the method or process comprises the step of combining or packaging a pharmaceutical composition comprising the VEGFR2-derived peptides and a pharmaceutically or physiologically acceptable carrier, together with one or more chemotherapeutic agents selected from the group consisting of gemcitabine, a pharmaceutically acceptable salt thereof, and a prodrug thereof. Alternatively, in another embodiment, the present invention also provides a use of a combination of the VEGFR2-derived peptides and one or more chemotherapeutic agents selected from the group consisting of gemcitabine, a pharmaceutically acceptable salt thereof, and a prodrug thereof, in manufacturing a kit for treating a cancer including pancreatic cancer.

In the above-mentioned embodiments of the present invention, a subject, in which a cancer is to be treated, may be HLA-A24-positive or HLA-A02-positive. The cancer to be treated includes pancreatic cancer.

EXAMPLES

Hereinafter, the present invention is described in detail with reference to Examples, more particularly to a clinical trial assaying the use of an epitope peptide that targets new tumor blood vessels in combination with gemcitabine for the treatment of unresectable advanced recurrent pancreatic cancer. However, materials, methods and such described therein only illustrate aspects of the invention and in no way are intended to limit the scope of the present invention. As such, materials, methods and such similar or equivalent to those described therein may be used in the practice or testing of the present invention.

Introduction

Herein described is a clinical trial of a novel vaccine chemotherapy method for unresectable advanced recurrent pancreatic cancer patients, in which Vascular Endothelial Growth Factor Receptor 2 (VEGFR2/KDR)-derived epitope peptides are mixed with Incomplete Freund's Adjuvant (IFA), then administered subcutaneously to the patients. The peptide vaccines are expected to show antitumor effects through inhibition of tumor neovascularization. They are used herein in combination with gemcitabine, the current standard for pancreatic cancer chemotherapy. The present clinical trial is intended to verify the safety of the novel vaccine chemotherapy aimed at inhibiting new tumor blood vessels and yielding anti-tumor effects through chemotherapy by performing a dose escalation of the administered epitope peptides in a cohort of three patients. The secondary purpose is to evaluate the response rate, survival time, and immune responses.

Surgical resection is the required therapy for curing pancreatic cancer; however, early detection is difficult and at the time of diagnosis, approximately 60% of the patients are in a situation where resection is not possible [Matsuno S et al. Int J Clin Oncol. 5:153-157, 2000., Pantalone D et al. 18:41-46, 2001.]. At present, gemcitabine is used as the standard therapy against unresectable pancreatic cancer; however, although the median survival period and the one-year survival rate have improved compared to groups administered with 5-FU alone, they are 5.7 months and 18% respectively and are by no means satisfactory. Furthermore, the response rate is 5.4% to 14.3% which is not high [Burns H A et al. J. Clin Oncol. 15: 2403-2413, 1997., Casper E S et al. 12:29-34, 1994., Carmichael J et al. Br J Cancer.; 73:101-105, 1996., Rothenberg M L et al. Ann Oncol. 7: 347-53, 1996.], and there is a need to examine novel therapeutic methods that may improve the response rate and survival period by a combined use with gemcitabine.

On the other hand, in recent years, the mechanism by which T cells recognize antigens has been elucidated, and in addition, proteins recognized by CTLs as tumor antigens have been discovered, and investigations on therapeutic methods using tumor antigens or the antigen genes have started. Immunotherapy using this identified tumor rejection antigen peptide was quickly adopted for malignant melanoma, and achievements have been reported since 1998 mainly by Rosenberg et al. [Celis E. et al. Cancer Biology 6:329-336, 1995., Marchard M, et al. Int. J. Cancer 63:883-885, 1995.]. Thereafter, combined use with IL-2 or GM-CSF, development of protocols for administering a plurality of tumor rejection antigen peptides, development of modified peptides, and clinical trials of peptide pulse dendritic cells have been carried out, and antitumor immunotherapy using tumor rejection antigen peptides is receiving attention even to date as a therapeutic method that complements conventional therapeutic methods such as surgical operation and chemotherapy.

Tumor antigens recognized and attacked by cytotoxic T cells (CTLs) were found, and thereafter, tumor-specific antigens were identified one after another and clinical trials for cancer vaccine therapy using epitope peptides, which is a specific immunotherapy targeting these antigens, are in progress. However, new problems have also been revealed. Even if potent CTLs can be induced, decreased or lost expression of MHC molecules in tumor cells, lack of target molecules in the tumor cells, and such may cause the loss of the CTL antitumor effects. Furthermore, the tumor antigen peptides that are identified to date are present in certain types of tumors, but they do not encompass all tumors. Therefore, to overcome these problems, the target cells of CTLs in vaccine therapy were set to tumor neovascular endothelial cells instead of the tumor cells themselves, and vaccine therapy targeting new tumor blood vessel-derived molecules was formulated. As the target molecule, attention was focused on Vascular Endothelial Growth Factor Receptor 2 (VEGFR2/KDR) which is hardly expressed in normal endothelial cells, but is highly expressed in tumor neovascular endothelial cells, and is a vascular endothelial cell growth factor receptor indispensable for the growth of these cells.

VEGFR2 is known to be expressed in the tumor tissues of many solid tumors such as breast cancer, colon cancer, kidney cancer, malignant melanoma, and lung cancer [Folkman J. Nature Biotechnol. 15, 510, 1997., Folkman J. EXS 79, 1-8, 1997.]. VEGFR2 expression has also been revealed to be strongly related to cancer cell proliferation [Kranz A, et al. Int J Cancer 84: 293-298, 1999., Nakopoulou L, et al. Hum Pathol 33:863-870, 2002., Reden L, et al. Breast Cancer Res. and Treat. 82:147-154, 2003.].

On the other hand, regarding whether or not VEGFR2 may become a target for immunotherapy, results of basic research on vaccination with VEGFR2 protein and DNA showed that antitumor effects were recognized through suppression of new tumor blood vessels regardless of the type of tumor; thus, it was confirmed that VEGFR2-specific cytotoxic T cells are responsible for this antitumor effect. The above showed that VEGFR2 may become a target for tumor immunotherapy [Yiwen, Li. et al. J. Exp. Med. 195, 1575-1584, 2002. Niethammer, A. G. et al. Nature Med. 8, 1369-1375, 2002.]. Furthermore, as a result of our basic analysis in humans, the presence of CTL clones that recognize and damage VEGFR2 was proven, and several types of HLA-A24 or A02 restricted epitope peptides capable of inducing potent CTLs were identified. CTLs induced by these epitope peptides damaged cultured human umbilical vein endothelial cells (HUVEC) that endogenously express VEGFR2 in a HLA-restricted manner. Furthermore, in the examination of in vivo antitumor effects using A2/Kb transgenic mice expressing with HLA, strong antitumor effects regardless of the type of cancer were confirmed through cancer vaccine therapy using VEGFR2-derived epitope peptides. Since CTLs could also be induced from cancer patient peripheral blood using peptides used in the present clinical trial, CTL precursor cells were found to exist in cancer patients as well [Wada S, Cancer Res. 65, 4939-4946, 2005.]. According to the above, by administering the present peptides and by inducing VEGFR2-specific CTLs in patients, tumor neovascularization can be inhibited, and potent antitumor effects may be obtained.

Thus, a new vaccine chemotherapy was devised, in which a peptide vaccine expected to show antitumor effects through inhibition of tumor neovascularization is used in combination with gemcitabine which is currently standard chemotherapy against pancreatic cancer. RFVPDGNRI (SEQ ID NO: 1), VYSSEEAEL (SEQ ID NO: 2), GYRIYDVVL (SEQ ID NO: 3), SYMISYAGM (SEQ ID NO: 4), KWEFPRDRL (SEQ ID NO: 5), DFLTLEHLI (SEQ ID NO: 6), AMFFWLLLV (SEQ ID NO: 7), VIAMFFWLL (SEQ ID NO: 8), AVIAMFFWL (SEQ ID NO: 9), KLIEIGVQT (SEQ ID NO: 10), YMISYAGMV (SEQ ID NO: 11), IQSDVWSFGV (SEQ ID NO: 12), or VLAMFFWLL (SEQ ID NO: 13) [Wada S, Cancer Res. 65, 4939-4946, 2005., WO2004/024766] which are derived from VEGFR2 and are HLA-A24 or HLA-A02 restricted epitope peptides are used in the vaccine formulation for combined use.

A summary of the rationale is the following:

1. VEGFR2 is an important molecule involved in the growth of tumor neovascular endothelial cells, and this peptide can be used to induce specific CTLs in vitro [Wada S, Cancer Res. 65, 4939-4946, 2005., WO2004/024766].

2. Specific CTLs can be induced in vitro also from cancer patient peripheral blood mononuclear cells using VEGFR2-derived HLA-A24 or HLA-A02 restricted epitope peptides [Wada S, Cancer Res. 65, 4939-4946, 2005.].

3. Most Japanese carry HLA-A24 or HLA-A02 [Date Y, et al. Tissue Antigen, 47, 93-101, 1996.].

4. These are biochemically stable and are suitable for clinical trials [Wada S, Cancer Res. 65, 4939-4946, 2005.].

5. Gemcitabine has already been approved as a chemotherapeutic agent against pancreatic cancer.

6. Gemcitabine is known to enhance immunocompetence such as CTL inducibility [Correale P, et al. J Immunol. 175, 820-828, 2005., Dauer M, et al. J Immunother. 28, 332-342, 2005.], and effects from combined use with vaccine formulations can be expected.

The present clinical trial was performed based on the above-mentioned rationale.

Materials and Methods

Subjects:

Subject patients were selected according to the following selection criteria and exclusion criteria.

Selection Criteria:

1. Primary pancreatic cancer for which radical resection was judged to be impossible due to: distant metastasis such as liver metastasis, peritoneal metastasis, and bone metastasis from various diagnoses such as image diagnoses by CT or ultrasound examination; distant lymph node metastasis as defined by the Japan Pancreas Society-edited Classification of Pancreatic Carcinoma, 5th Ed; or infiltration into the great vessels (abdominal aorta, proper hepatic artery, left and right hepatic arteries, superior mesenteric artery, and superior mesenteric veins that cannot be reconstructed); or recurrent pancreatic cancer.

2. While the presence or absence of lesions measurable by RECIST is no object, assessment of the clinical effects on the tumor must be possible.

3. An ECOG performance status of 0 to 2.

4. An age of 20 or higher and 80 or lower at the time of obtaining consent.

5. The expected life prognosis must be three months or more at the start of the gemcitabine and vaccine therapy.

6. If the patient has received some kind of operation, the patient should have recovered from the effects of the operation. Alternatively, four weeks or more must have elapsed since the previous therapy.

7. Functions of the major organs must be maintained: bone marrow function (white blood cell count of 2000/mm$^3$ or more and 15000/mm$^3$ or less, and platelet count of 7.5/mm$^3$ or more); hepatic function (GOT of 150 IU/L or less, GPT of 150 IU/L or less, and T-bil 3.0 g/dL or less); and renal function (Cr of 3.0 or less).

8. Presence of suitable HLA.

9. No history of treatment using gemcitabine against the primary disease.

Exclusion Criteria:

1. Pregnant women (women capable of becoming pregnant are to take contraceptive measures after the start of this clinical study).

2. Nursing women (nursing is to be stopped after the start of this clinical study).

3. Patients intending to become pregnant (appropriate contraceptive measures are to be taken by both men and women during the trial period).

4. Patients having active infection that is difficult to regulate.

5. Patients for whom the following pharmaceutical agents must be administered during the trial:

systemic administration of adrenal steroid agents; or systemic administration of immunosuppressive agents.

6. Patients having uncontrolled double cancer.

7. Patients having traumatic lesions that have not yet healed.

8. Patients suspected of having intestinal paralysis or interstitial pneumonia.

9. Patients determined by a physician or a principle physician to be inappropriate.

Treatment Plan:

Selection of Subject Cancer Patients:

Subject patients were those carrying suitable HLA and having primary pancreatic cancer for which radical resection was judged to be impossible or having recurrent pancreatic cancer. Cases where pancreatic cancer was most highly suspected by image diagnosis were also included in the subject patients.

Method for Examining HLA Expression:

Outside examination was requested to SRL, Inc (Tokyo).

Dose of Gemcitabine:

1,000 mg/m$^2$ of gemcitabine (gemcitabine HCl), which is the standard of care dosage and administration approved for insurance coverage, was administered for three weeks followed by one week of no administration.

Dose and Method for Administering the Peptides and Adjuvant:

0.5 mg, 1 mg, and 2 mg of the synthesized peptide were mixed with 0.5 mL, 1 mL, and 2 mL of incomplete Freund's adjuvant (MONTANIDE*ISA51VG, SEPPIC, France), respectively, and administered subcutaneously to the underarm or near the inguinal area of the patients.

Administration Schedule:

The schedule is shown in FIG. 1. One course was set to 28 days from the start of the initial administration.

Dose Escalation Method and Three-Patient Cohort:

The dosage and administration of gemcitabine (1,000 mg/m$^2$, three weeks of administration and one week of no administration) were fixed, and vaccine administration was dose escalated in terms of peptide dose to 0.5 mg, 1 mg, and 2 mg. Specifically, 0.5 mg of peptide is administered to three patients. If not a single individual shows undeniably correlated hematologic toxicity of Grade 4 (NCI-CTC version 3.0) or higher (excluding nausea/vomiting) or hematologic toxicity of Grade 3 (NCI-CTC version 3.0) or higher, the peptide at the next dose (1 mg) is administered to the three patients. If side effects are expressed in two or more individuals, this clinical trial is discontinued. If side effects are expressed in one individual, three more patients are additionally registered at the same dose, and if side effects are expressed in one case out of the six cases, the trial moves on to the next dose. If side effects are observed in even one individual at this stage, the present clinical trial is discontinued. Dose escalation from 1 mg to 2 mg was carried out in the same manner.

Quality Control:

Regarding the administered peptide, cGMP grade peptides (Neo-MPS, San Diego) were a gift from Human Genome Center, Institute of Medical Science, University of Tokyo. Regarding the adjuvant, GMP grade-compliant incomplete Freund's adjuvant (MONTANIDE*ISA51VG) was purchased from SEPPIC Co., France. Storage of the peptides and preparation of the peptide vaccines were carried out at the Pharmaceutical Department of Wakayama Medical University Hospital.

Regarding the "Preliminary Test Administration":

For the purpose of avoiding unanticipated adverse events, such as anaphylactic shock, 10 mg of the peptide is subcutaneously administered as a preliminary test administration before the first vaccine administration to a site other than the site of the actual administration, and monitoring is carried out for 30 minutes. If a Grade 3 or higher local reaction or systemic adverse event could not be observed, the actual administration was carried out. With regard to the "preliminary test administration", local adverse event and systemic adverse event were not observed in any of the cases.

Results

Evaluation of the Trial Data:

Safety Evaluation:

Safety evaluation targeted patients who have received at least one administration of gemcitabine and the peptides. The presence and degree of adverse events were determined by referring to the National Cancer Institute-Common Toxicity Criteria, (NCI-CTC) (Japanese translation JCOG edition) version 3.

Immunological Evaluation:

Before vaccine administration, 50 mL of peripheral blood was collected after completion of each course (Day 28 after the initial administration), and peripheral blood mononuclear cells (PBMC) were separated and measured by Ficoll-paque density centrifugation.

Analysis of CTL Reaction:

The CTL reaction resulting from the administered peptides was measured using IFN-gamma ELISPOT assay (ELISPOT Human IFN-gamma set, BD). More specifically, Stimulator was prepared by pulsing VEGFR2-169 (SEQ ID NO: 1) and HIV-A24 peptides into A24-LCL (HLA-A*2402-positive), and HIV peptide was used as the negative control. The assay was performed three wells at a time for each of R/S ratio and Stimulator and the average value was calculated in terms of the number of spots per single well. The number of spots was read on an ELISPOT reader (IMMUNO SPOT, Cellular Technology Ltd.). The value obtained by subtracting the number of spots from HIV pulsing from the number of spots from VEGFR2-169 pulsing was taken to be the specific IFN-gamma production spots with respect to VEGFR2-169 (Specific Spots). If an increase in the specific IFN-gamma production spots was observed after one course and after two courses, it was considered that there has been an immune response due to vaccine administration.

Population Analysis of CD8-Positive T Cells (FIG. 2):

Whether there is a change in the proportion of each of the fractions of naive, memory, effector memory, and effector T cells among CD8-positive T cells was analyzed by flow cytometry (FACS Calibur, BD) with four color staining. As shown in FIG. 2, the lymphocyte fraction of PBMC was gated, and the CD8-positive fraction was gated. The CD8-positive fraction was further developed using CD27(BD) and CD45RA (SD) to obtain the effector fraction (CD27-negative/CD45RA-positive), the effector memory fraction (CD27-negative/CD45RA-negative), the memory fraction (CD27-positive/CD45RA-negative), and the naive fraction (CD27-positive/CD45RA-positive). At the same time, the functional lymphocyte fractions were determined by perforin staining (Cytofix/Cytoperm kit, BD).

Analysis of Regulatory T Cells (FIG. 3):

CD25high and Foxp3-positive cells among CD4-positive T cells were specified as regulatory T cells and their numerical change before and after vaccine administration was measured by flow cytometry (FACS Calibur, BD) after four color staining. More specifically, as in FIG. 3, lymphocyte fraction of PBMC was gated, and after development using CD4 and CD25, the proportion of CD25high and Foxp3-positive cells (Human Regulatory Staining kit, eBioscience) among CD4-positive T cells was calculated.

Clinical Efficacy Evaluation:

Cytoreductive Effects

Patients who have completed at least one course defined by the present protocol were chosen as subjects. For tumors that can be determined by images, clinical effects were evaluated after the final vaccination in each course, mainly according to "New Guidelines to Evaluate the Effect of Treatment in Solid Tumors (RECIST guideline Version 2) Japanese Translation, JCOG Edition". Even in cases where the four-week period is not fulfilled at the time of clinical evaluation, they were noted as objective responses and their clinical significance was evaluated as reference data. CT and PET were used for the anti-tumor effect evaluation.

Survival Time:

A long-term follow-up observation was performed, and the survival time and survival rate were investigated.

Patient Results;

Three people took part at each level, and safety evaluation became possible. The cases as of July 31 are summarized in Table 1 (see below).

Case 1 (Level I/0.5 mg)

Case 1 is a sixty-eight-year-old female who was previously treated with chemotherapy using TS-1, became unresponsive, and registered thereafter in the instant trial. Two courses were carried out but systemic adverse events were absent, and local adverse events at the site of vaccination were also absent (Table 1, see below). Image assessment was PD. Tumor markers also increased. According to immunologic monitoring, specific CTL reaction against the administered peptide was not observed (Table 2, see below). Before vaccination, it was within the normal range of regulatory T cells (normal average is 3.9+/−1.2%), but an increase beyond the normal range was observed after one course and also after two courses (Table 6, see below). The patient died due to aggravation of the original disease 3.3 months after the initial vaccination.

Case 2 (Level I/0.5 mg)

Case 2 is a sixty-six-year-old male who received two vaccinations but was transferred to another hospital at his own request, and subsequently dropped out of the trial (Table 1, see below). Systemic adverse events were absent, and local adverse events at the site of vaccination were also absent.

Case 3 (Level I/0.5 mg)

Figure 5:
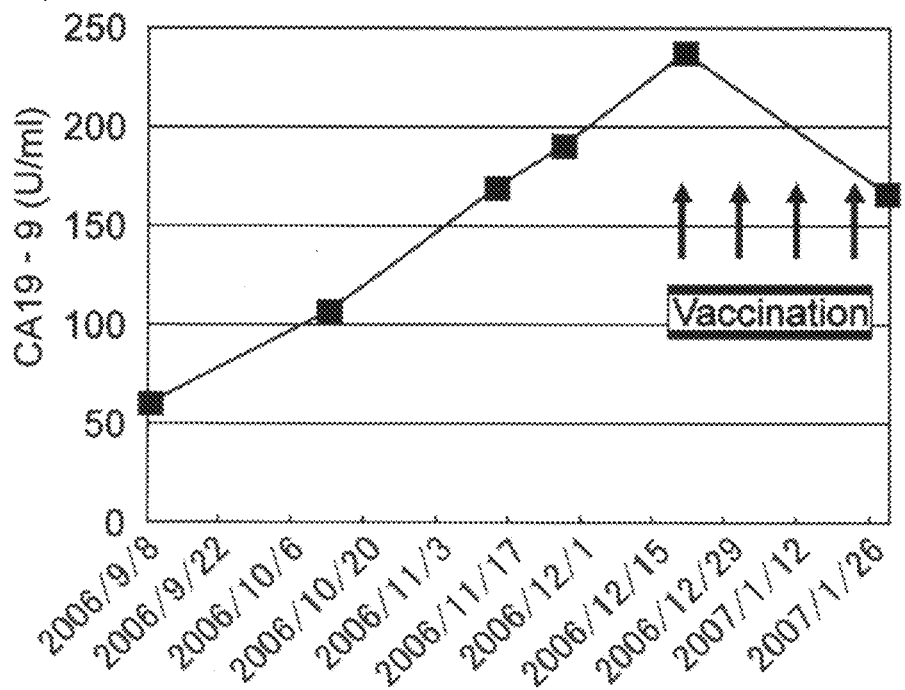
FIG. 5 presents the changes in tumor marker concentration over time in Case 3.
Figure 6:
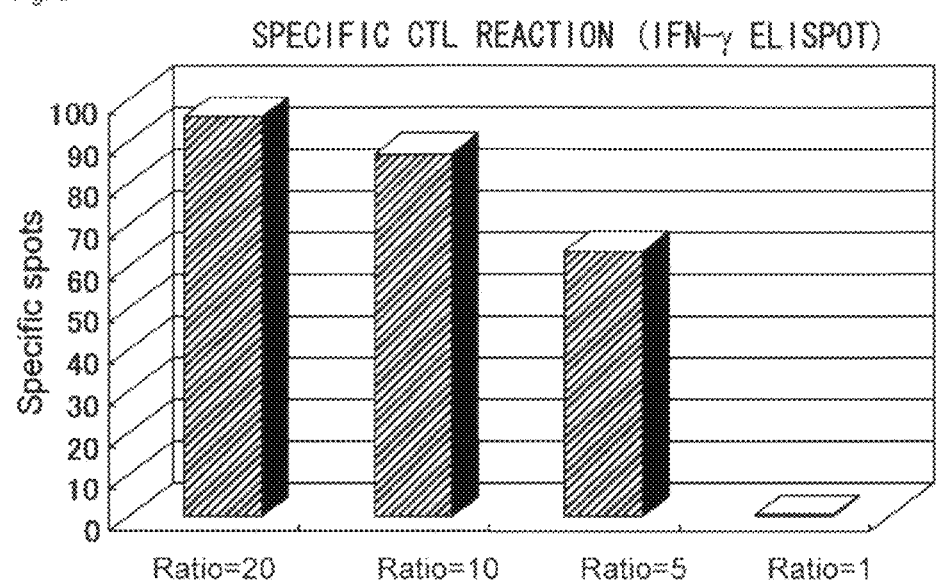
FIG. 6 presents the levels of specific CTL reaction arising in Case 3 before and after vaccination.

Case 3 is a sixty-four-year-old male. One course was carried out. Grade 3 neutropenia and hepatic dysfunction were observed as systemic adverse events (Table 1, see below). Withdrawal of gemcitabine for one week allowed recovery from both conditions, and administration was then continued. Grade 2 induration and redness at the site of inoculation were observed and lymphadenopathy (inguinal swelling) near the inoculation site was observed as local adverse events. Image showing strong accumulation was observed at the swollen site using PET (FIG. 4), and histopathologically strong inflammation was observed as a result of biopsy, suggesting at an immune response in response to peptide inoculation. Image assessment was SD and the tumor marker (CA19-9) decreased (FIG. 5). According to immunologic monitoring, specific CTL reaction against the administered peptides was observed (FIG. 6), and in CD8-positive T cell fraction analysis, an increase was observed in the Naive T cell fraction and the Effector T cell fraction (Table 3, see below). Regulatory T cells were above the normal range (normal average is 3.9+/−1.2%) before the start of vaccination, but decreased to the normal range after one course (Table 6, see below). Thereafter, the patient died due to aggravation of the original disease 7.3 months after the initial vaccination.

Case 4 (Level I/0.5 mg)

Figure 7:
FIG. 7 presents a series of CT scans on Case 4, depicting the reducing effect of the treatment on pancreatic cancer primary focus.
Figure 8:
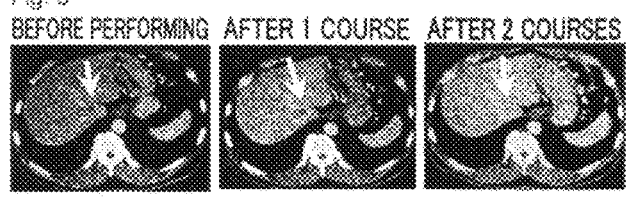
FIG. 8 presents a series of CT scans on Case 4, depicting the tumor reducing effect on pancreatic cancer liver metastatic focus 1.
Figure 9:
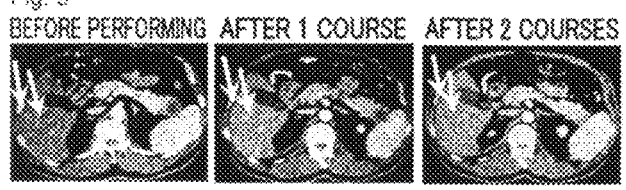
FIG. 9 presents a series of CT scans on Case 4, depicting the tumor reducing effect on pancreatic cancer liver metastatic focus 2.
Figure 10:
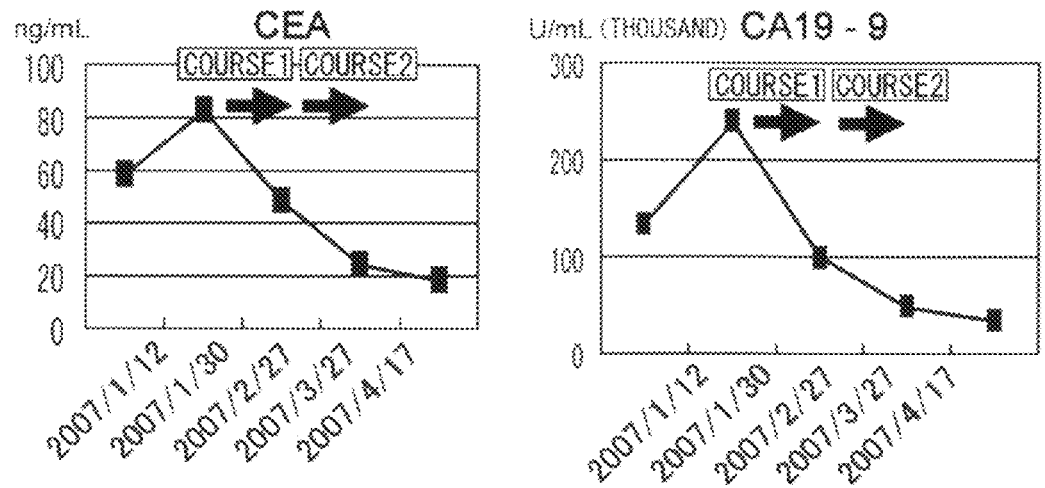
FIG. 10 presents the changes in the tumor markers, CEA and CA19-9, arising in Case 4 over the course of treatment.
Figure 11:
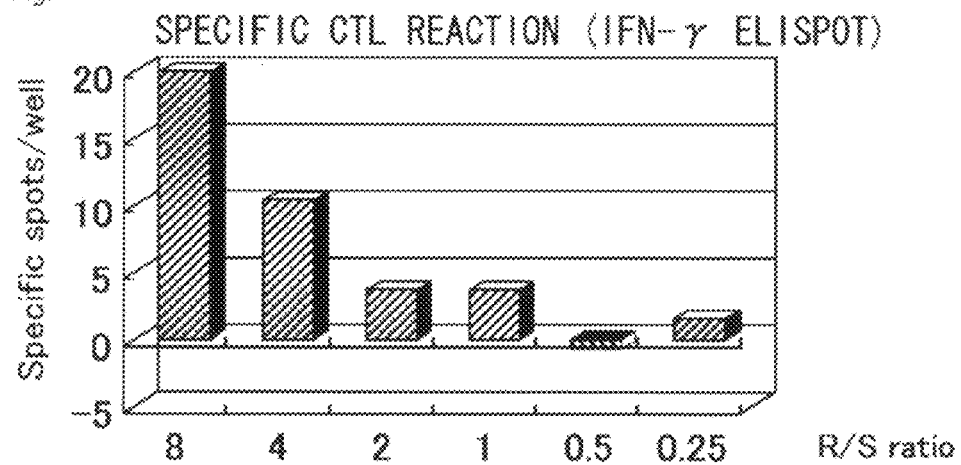
FIG. 11 presents the specific CTL reaction arising in Case 4 before and after vaccination.

Case 4 is a sixty-one-year-old male. Two courses were carried out. Systemic adverse events were absent, and as local adverse events, Grade 2 induration and redness were observed at the site of inoculation (Table 1, see below). Image assessment was Objective Response. More specifically, the primary focus in the pancreatic tail region was found to be SD after one course, and after two courses it was clearly reduced, and that effect was maintained for nearly two months (FIG. 7). Liver metastatic focus in the hepatic portal region became completely inapparent after two courses (FIG. 8). Liver metastatic focus near the gallbladder became inapparent after one course, and almost disappeared after two courses (FIG. 9). On the other hand, tumor markers (CA19-9 and CEA) which were at high levels before vaccination decreased after one course and after two courses, and the decreasing trend of the tumor markers continued even one month later (FIG. 10). According to immunologic monitoring, specific CTL reaction against the administered peptides was observed (FIG. 11). Regulatory T cells were within the normal range before the start of vaccination, after one course, and after two courses (Table 6, see below). 6.3 Months since the first vaccination the subject was alive.

Case 5 (Level II/1 mg)

Case 5 is a sixty-five-year-old male. Two courses were carried out. Systemic adverse events and local adverse events were absent (Table 1, see below). Image assessment was PD. Tumor markers also increased. According to immunologic monitoring, specific CTL reaction against the administered peptides was observed (Table 2, see below), and in CD8-positive T cell fraction analysis, an increase was observed in the naive T cell fraction and effector T cell fraction (Table 4, see below). Regulatory T cells were within the normal range before the start of vaccination, after one course, and after two courses (Table 6, see below). Thereafter, the patient died due to aggravation of the original disease 4.5 months after the initial vaccination.

Case 6 (Level II/1 mg)

Figure 12:
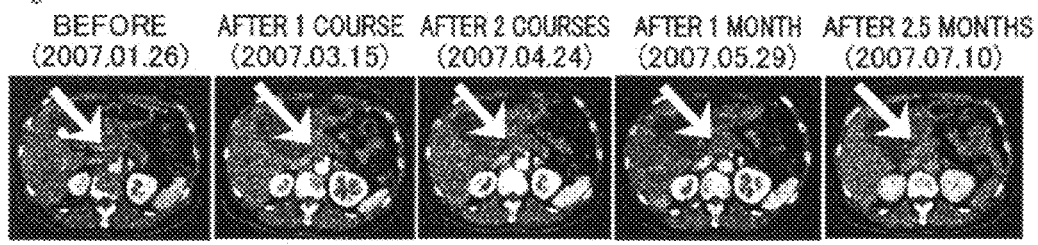
FIG. 12 presents a series of CT scans on Case 6, depicting the tumor reducing effect on pancreatic cancer primary focus.
Figure 13:
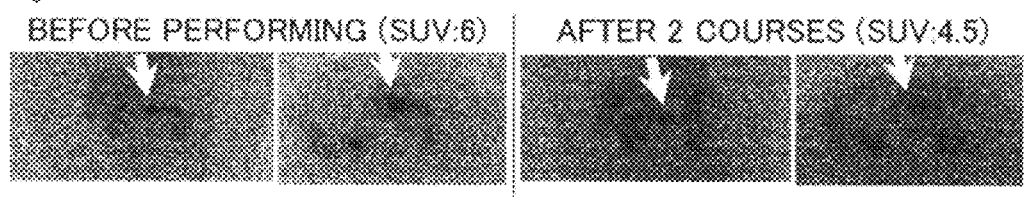
FIG. 13 presents a series of PET scans on Case 6, depicting the tumor reducing effect on pancreatic cancer primary focus.
Figure 14:
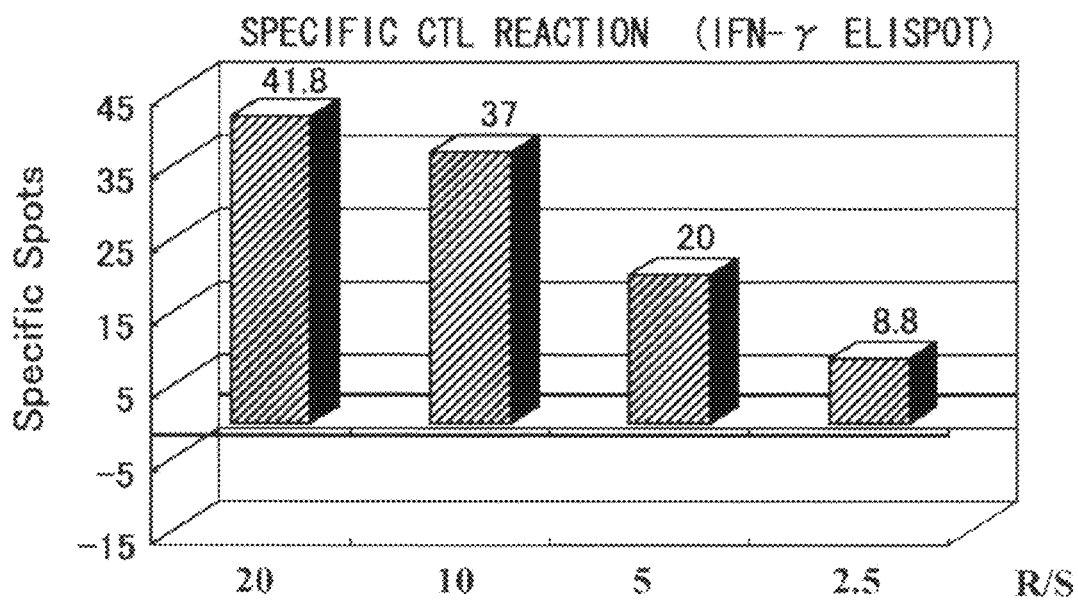
FIG. 14 presents the specific CTL reaction arising in Case 6 before and after vaccination.

Case 6 is a fifty-seven-year-old female. Two courses were carried out. Grade 3 neutropenia was observed as the systemic adverse event (Table 1, see below). Withdrawal of GEM for one week allowed recovery, and administration was then continued. Grade 2 induration and redness at the site of inoculation were observed and lymphadenopathy (inguinal swelling) near the inoculation site were observed as local adverse events. Image assessment was Objective Response. More specifically, the primary focus in the pancreatic head region was reduced after two courses, and this effect was maintained for nearly 2.5 months (FIG. 12). PET Scans obtained before vaccination and after completion of two courses were compared. Accumulation to the tumor clearly decreased after two courses (FIG. 13). By comparing SUV values which objectively indicate the amount of accumulation to the tumor, the decrease from 6 to 4.5 clearly suggested that there has been an antitumor effect. Furthermore, the tumor marker (tumor markers other than DUPAN2 were normal from the time of registration) decreased from after two courses, and the decreasing effects continued even two months later (Table 7, see below). According to immunologic monitoring, specific CTL reaction against the administered peptides was observed (FIG. 14), and in CD8-positive T cell fraction analysis, an increase was observed in the Naive T cell fraction and a decrease was observed in the Effector T cell fraction (Table 4, see below). Regulatory T cells were within the normal range before the start of vaccination, after one course, and after two courses (Table 6, see below). At six months after the first vaccination, the QOL remained good and the subject was alive.

Case 7 (Level II/1 mg)

Figure 15:
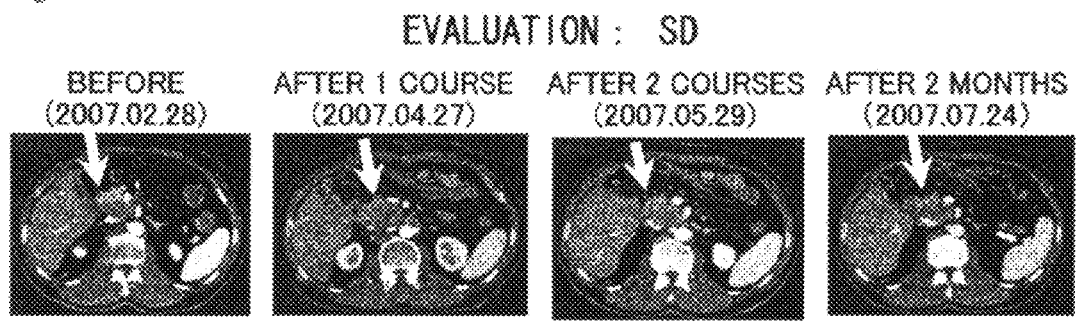
FIG. 15 presents a series of CT scans on Case 7, depicting changes in pancreatic cancer primary focus.
Figure 16:
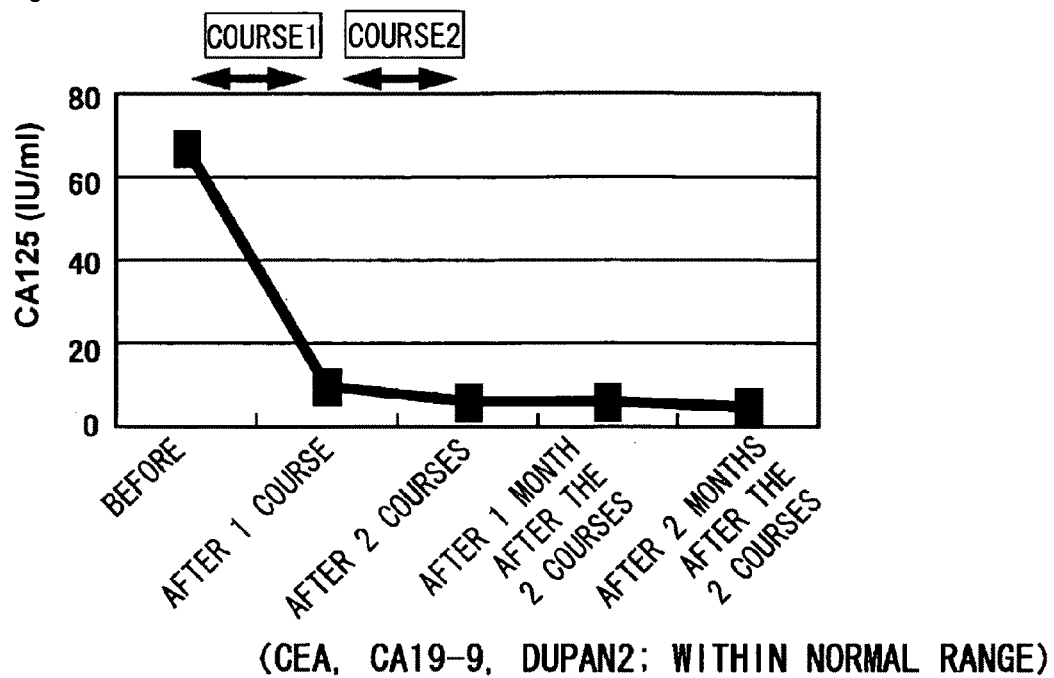
FIG. 16 presents the changes in the tumor marker CA125 arising in Case 7 over the course of treatment.
Figure 17:
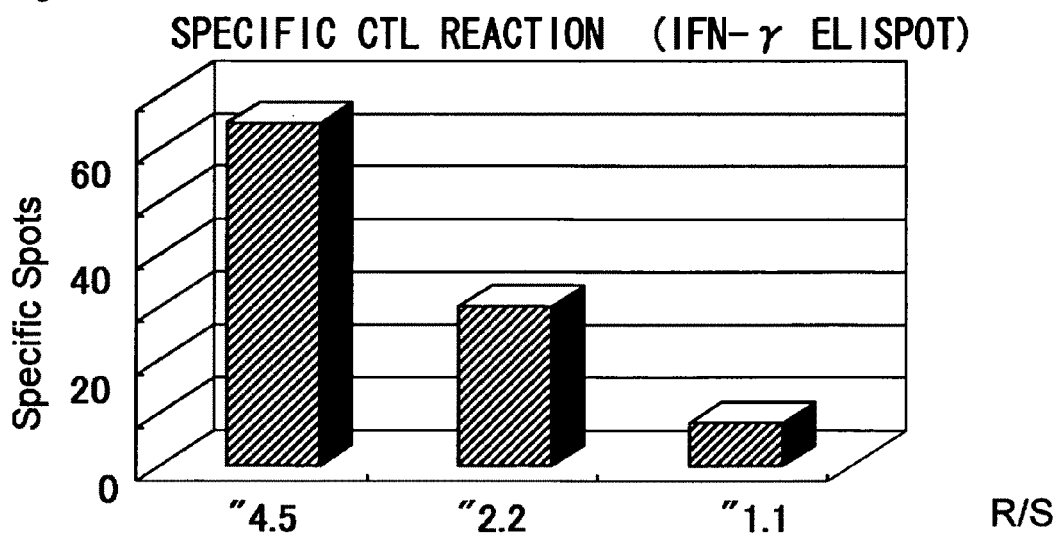
FIG. 17 presents the specific CTL reaction arising in Case 7 before and after vaccination.

Case 7 is a sixty-nine-year-old male. Two courses were carried out. Grade 3 neutropenia was observed as the systemic adverse event (Table 1, see below). Withdrawal of GEM for one week allowed recovery, and administration was then continued. Grade 2 induration and redness at the site of inoculation were observed and lymphadenopathy (inguinal swelling) near the inoculation site was observed as local adverse events. Image assessment was SD (FIG. 15). More specifically, the primary focus in the pancreatic head region did not show any change in size after two courses, and this effect was maintained for nearly two months (FIG. 15). Furthermore, the tumor marker (tumor markers other than CA125 were normal from the time of registration) decreased after one course, and the decreasing effects continued even two months later (FIG. 16). According to immunologic monitoring, specific CTL reaction against the administered peptides was observed (FIG. 17), and in CD8-positive T cell fraction analysis, a decrease was observed in the Naive T cell fraction and an increase was observed in the Effector T cell fraction (Table 4, see below). Regulatory T cells were within the normal range before the start of vaccination, after one course, and after two courses (Table 6, see below). At 4.3 after the first vaccination, the QOL remained good and the subject was alive.

Case 8 (Level III/2 mg)

Case 8 is a fifty-eight-year-old male. One course was completed, and while the second course was being carried out, gastrointestinal bleeding occurred from the enlarged tumor. The cause was judged to be enlargement of the tumor, and the trial was discontinued (Table 1, see below). Hepatic dysfunction was observed as the systemic adverse event. Local adverse events were absent. Image assessment as of the completion of one course was PD. The tumor markers also increased.

Case 9 (Level III/2 mg)

Case 9 is a seventy-three-year-old male. After one administration, the study was deferred due to gastrointestinal constriction caused by enlargement of the tumor (Table 1, see below).

Case 10 (Level III/2 mg)

Figure 18:
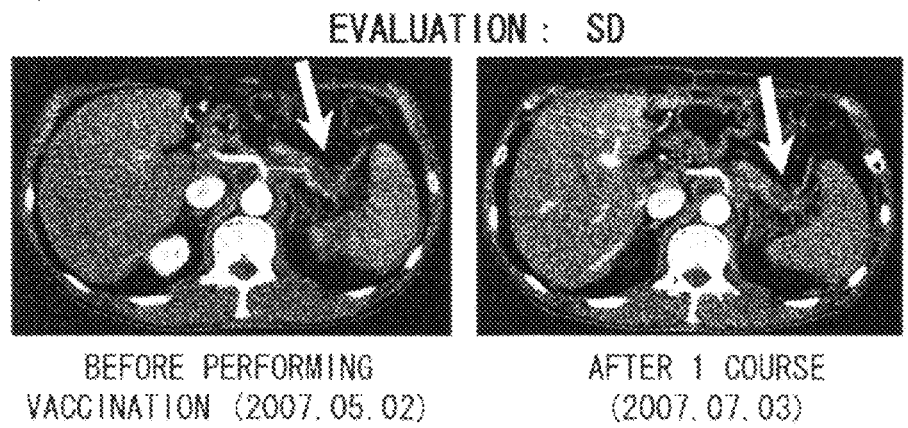
FIG. 18 presents a series of CT scans on Case 10, depicting the changes in pancreatic cancer primary focus.
Figure 19:
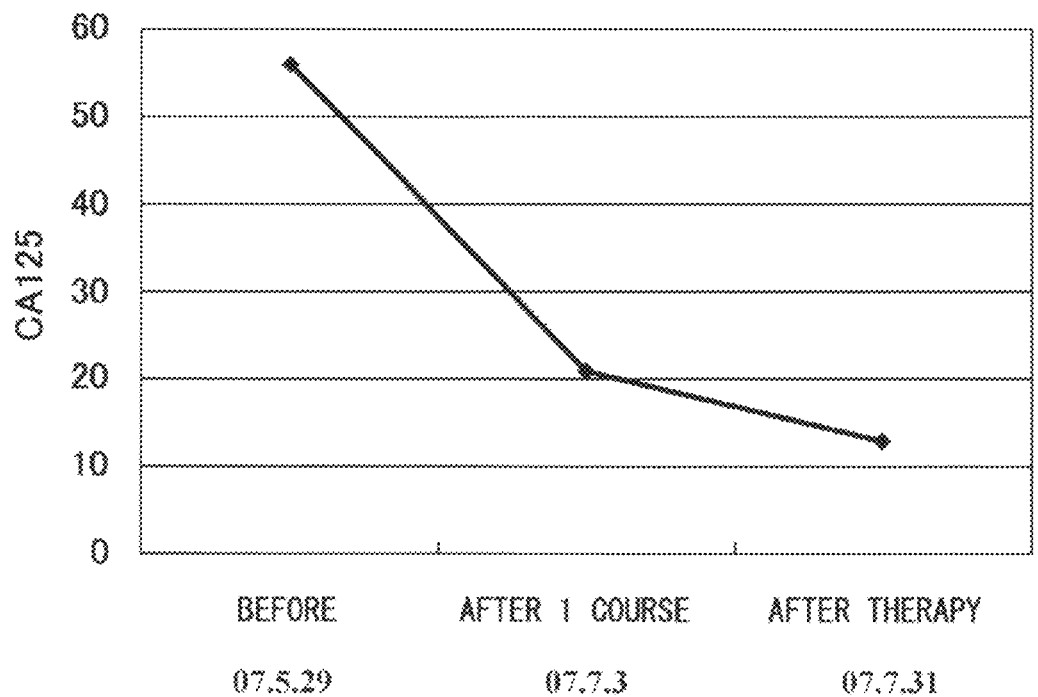
FIG. 19 presents the changes in the tumor marker CA125 arising in Case 10 over the course of treatment.

Case 9 is a sixty-two-year-old male. One course was carried out. Systemic adverse events were absent, and as local adverse events, induration and redness of Grade 2 or less were observed (Table 1, see below). Image assessment was SD (FIG. 18). Further, the tumor marker (tumor markers other than CA125 were normal from the time of registration) decreased, and the decrease in the tumor marker continued for approximately one month (FIG. 19). According to immunologic monitoring, specific CTL reaction against the administered peptides was observed (Table 2, see below), and in CD8-positive T cell fraction analysis, an increase was observed in the Naive T cell fraction and a decrease was observed in the Effector T cell fraction (Table 5, see below). Regulatory T cells were at a high value of 6.4 before the start of vaccination, but decreased to a normal range at 2.1 after one course (Table 6, see below).

Comparison with Gemcitabine Alone

In Table 8 (see below), from the viewpoint of antitumor effects in the cases and the viewpoint of DTH reaction which is one of the immune responses, comparison with data obtained so far with gemcitabine alone was carried out. Antitumor effects were compared in terms of disease control rate (number of CR+number of PR+number of SD/all cases) and clear antitumor effect expression rate (objective response). While the rate stayed at 45% to 48% with GEM alone, the rate greatly surpassed at 62.5% with this protocol. The objective response also surpassed by two fold or more. DTH reaction, which is one of the immune responses, was observed highly frequently. Since it is hardly observed with VEGFR2 alone (personal communication), Gemcitabine was considered to be enhancing the immune responses. In fact, in cases where DTH reaction took place, reactions of SD or higher have been obtained clinically, and PD cases and cases in which DTH was absent matched completely. Therefore, cases in which some kind of immune response is evoked are considered to be clinically effective as well.

Tables

TABLE 1

| | | | | | |
|---|---|---|---|---|---|
| | | | Summary of the clinical trial cases | | |
| CASES | PEPTIDES | AGE/ GENDER | VACCINATION STATUS | SYSTEMIC ADVERSE EVENTS | LOCAL ADVERSE EVENTS |
| 1 | LEVEL I 0.5 mg | 68/ FEMALE | COMPLETED 2 COURSES | NONE | NONE |
| 2 | | 66/ MALE | D/O (2 ADMINISTRATIONS) | NONE | NONE |
| 3 | | 64/ MALE | COMPLETED 1 COURSE | NEUTROPENIA/ HEPATIC INJURY | INDURATION/ REDNESS/ LYMPHADE- NOPATHY |
| 4 | | 61/ MALE | COMPLETED 2 COURSES | NONE | INDURATION/ REDNESS |
| 5 | LEVEL II 1 mg | 65/ MALE | COMPLETED 2 COURSES | NONE | NONE |
| 6 | | 57/ FEMALE | COMPLETED 2 COURSES | NEUTROPENIA | INDURATION/ REDNESS/ LYMPHADE- NOPATHY |
| 7 | | 69/ MALE | COMPLETED 2 COURSES | NEUTROPENIA | INGUINAL SWELLING |
| 8 | LEVEL III 2 mg | 58/ MALE | DURING COURSE 2 | NEUTROPENIA/ TUMOR HEMORRHAGE | NONE |
| 9 | | 73/ FEMALE | (1 ADMINISTRATION) | DEFERRED DUE TO GASTROINTESTINAL CONSTRICTION FOLLOWING TUMOR ENLARGEMENT | |
| 10 | | 62/ MALE | COMPLETED 1 COURSE | NONE | INDURATION/ REDNESS |

| CASES | PEPTIDES | EVALUABLE LESIONS | EVALUATION | TUMOR MARKERS | OBSERVATION PERIOD, SURVIVAL |
|---|---|---|---|---|---|
| 1 | LEVEL I 0.5 mg | PRIMARY FOCUS | PD | INCREASED | 3.3 mo, DECEASED |
| 2 | | | | | |
| 3 | | PRIMARY FOCUS | SD | DECREASED | 7.3 mo, DECEASED |
| 4 | | PRIMARY/ LIVER METASTATIC FOCUS | OBJECTIVE R | DECREASED | 6.3 mo, ALIVE |
| 5 | LEVEL II 1 mg | PRIMARY FOCUS | PD | INCREASED | 4.5 mo, DECEASED |
| 6 | | PRIMARY FOCUS | OBJECTIVE R | DECREASED | 6.0 mo, ALIVE |
| 7 | | PRIMARY FOCUS | SD | DECREASED | 4.3 mo, ALIVE |
| 8 | LEVEL III 2 mg | PRIMARY FOCUS | PD | INCREASED | 3.7 mo, ALIVE |
| 9 | | PRIMARY/ LIVER METASTATIC FOCUS | | | 2.8 mo, ALIVE |
| 10 | | PRIMARY FOCUS | SD | DECREASED | 2.4 mo, ALIVE |

TABLE 2

The specific CTL reaction/DTH reaction against the administered peptides

|  |  | BEFORE ADMINISTRATION | AFTER ADMINISTRATION | DTH REACTION | CLINICAL EVALUATION |
|---|---|---|---|---|---|
| LEVEL I 0.5 mg | CASE 1 | − | − | − | PD |
|  | CASE 3 | − | + | + | SD |
|  | CASE 4 | NT | + | + | Objective R |
| LEVEL II 1 mg | CASE 5 | − | + | − | PD |
|  | CASE 6 | − | + | + | Objective R |
|  | CASE 7 | − | + | + | SD |
| LEVEL III 2 mg | CASE 8 | NT | NT | − | PD |
|  | CASE 9 | NT |  |  | NT |
|  | CASE10 | − | + | + | SD |

※NT: NOT TESTED

TABLE 3

Analysis of the Level I CD8-positive T cell fractions

|  |  | BEFORE ADMINISTRATION | AFTER 1 COURSE | AFTER 2 COURSES | CLINICAL EVALUATION |
|---|---|---|---|---|---|
| CASE 1 | Naive/CD8+ (%) |  | NT |  | PD |
|  | Memory/CD8+ (%) |  |  |  |  |
|  | E. Memory/CD8+ (%) |  |  |  |  |
|  | Effector/CD8+ (%) |  |  |  |  |
| CASE 3 | Naive/CD8+ (%) | 12.5 | 16.9 |  | SD |
|  | Memory/CD8+ (%) | 11.8 | 10.9 |  |  |
|  | E. Memory/CD8+ (%) | 3.7 | 2.4 |  |  |
|  | Effector/CD8+ (%) | 60.9 | 64.0 |  |  |
| CASE 4 | Naive/CD8+ (%) |  | NT |  | Objective R |
|  | Memory/CD8+ (%) |  |  |  |  |
|  | E. Memory/CD8+ (%) |  |  |  |  |
|  | Effector/CD8+ (%) |  |  |  |  |

※ CASE 3: TERMINATED AFTER 1 COURSE.
NT: NOT TESTED

TABLE 4

Analysis of the Level II CD8-positive T cell fractions

|  |  | BEFORE ADMINISTRATION | AFTER 1 COURSE | AFTER 2 COURSES | CLINICAL EVALUATION |
|---|---|---|---|---|---|
| CASE 5 | Naive/CD8+ (%) | 0 | 11.9 | 3.9 | PD |
|  | Memory/CD8+ (%) | 0.1 | 11.5 | 8.8 |  |
|  | E. Memory/CD8+ (%) | 21.5 | 22.3 | 24.3 |  |
|  | Effector/CD8+ (%) | 14.0 | 11.2 | 19.2 |  |
| CASE 6 | Naive/CD8+ (%) | 54.3 | 64.5 | 69.3 | Objective R |
|  | Memory/CD8+ (%) | 25.8 | 22.1 | 20.6 |  |
|  | E. Memory/CD8+ (%) | 1.2 | 0.4 | 0.3 |  |
|  | Effector/CD8+ (%) | 10.2 | 5.9 | 3.9 |  |
| CASE 7 | Naive/CD8+ (%) | 9.4 | 1.1 | 0.1 | SD |
|  | Memory/CD8+ (%) | 4.4 | 0.1 | 0 |  |
|  | E. Memory/CD8+ (%) | 10.6 | 12.0 | 8.3 |  |
|  | Effector/CD8+ (%) | 14.4 | 17.8 | 18.0 |  |

TABLE 5

Analysis of the Level III CD8-positive T cell fractions

|  |  | BEFORE ADMINISTRATION | AFTER 1 COURSE | AFTER 2 COURSES | CLINICAL EVALUATION |
|---|---|---|---|---|---|
| CASE 8 | Naive/CD8+ (%) |  | NT |  | PD |
|  | Memory/CD8+ (%) |  |  |  |  |
|  | E. Memory/CD8+ (%) |  |  |  |  |
|  | Effector/CD8+ (%) |  |  |  |  |
| CASE 9 | Naive/CD8+ (%) |  | NT |  | NT |
|  | Memory/CD8+ (%) |  |  |  |  |
|  | E. Memory/CD8+ (%) |  |  |  |  |
|  | Effector/CD8+ (%) |  |  |  |  |

TABLE 5-continued

Analysis of the Level III CD8-positive T cell fractions

| | | BEFORE ADMINISTRATION | AFTER 1 COURSE | AFTER 2 COURSES | CLINICAL EVALUATION |
|---|---|---|---|---|---|
| CASE 10 | Naive/CD8+ (%) | 51.0 | 57.2 | | SD |
| | Memory/CD8+ (%) | 10.7 | 11.4 | | |
| | E. Memory/CD8+ (%) | 4.7 | 3.4 | | |
| | Effector/CD8+ (%) | 18.2 | 14.8 | | |

※ CASES 8 10: TERMINATED AFTER 1 COURSE.
NT: NOT TESTED

TABLE 6

Analysis CD4-positive/CD25-high/Foxp3-positive Regulatory T cells

| LEVELS | CASES | BEFORE | AFTER 1 COURSE | AFTER 2 COURSES | CLINICAL EVALUATION |
|---|---|---|---|---|---|
| I | 1 | 2.4 | 9.5 | 7.8 | PD |
| | 3 | 10.6 | 4.4 | | SD |
| | 4 | 3.2 | 2.2 | 1.5 | Objective R |
| II | 5 | 4.6 | 2.3 | 1.8 | PD |
| | 6 | 3.1 | 3.9 | 4.1 | Objective R |
| | 7 | 3.1 | 3.3 | 3.1 | SD |
| III | 8 | N.T. | N.T. | | PD |
| | 9 | N.T. | N.T. | | N.T. |
| | 10 | 6.4 | 2.1 | | SD |

MEAN OF HEALTHY INDIVIDUALS (SD) . . .
CD4+CD25$^{high}$ Foxp3+: 3.9%(±1.2)

TABLE 7

The changes in tumor marker arising in Case 6 over the course of treatment

| | 1/26 4 WEEKS BEFORE PERFORMING | 2/8 BEFORE PERFORMING | 3/15 AFTER 1 COURSE | 4/24 AFTER 2 COURSES | 5/29 AFTER 1 MONTH | 6/26 AFTER 2 MONTHS |
|---|---|---|---|---|---|---|
| DUPAN2 | 1600< | 1600< | 1600< | 1200 | 960 | 880 |

(CEA, CA19-9, CA125; NORMAL RANGE)

TABLE 8

Summary of the antitumor effects and DTH reactions associated with the treatment of the instant invention

| | GEM alone | GEM + R2-169 (positive cases/ total cases) |
|---|---|---|
| Disease control rate (SD or higher) | 45-48% | 62.5% (5/8) |
| Evident tumor reducing effect (Objective Response) | 10% | 25% (2/8) |
| DTH reaction | N.T. | 62.5% (5/8) |

Discussion

There is no question that pancreatic cancer is intractable and is a tumor with the worst prognosis. At present, the only pharmaceutical therapy against pancreatic cancer is gemcitabine, but clinically, it is still unsatisfactory.

On the other hand, subsequent to identification of epitope peptides against tumor antigens, there has been great expectations for cancer vaccine therapy; however, it is a well known fact that the clinical performance to date have fallen short of such expectations. The main reason is the low expression or lack of MHC molecules in tumor cells. More specifically, even if strong CTLs are induced using vaccines, if there is a lack of MHC molecules, the antitumor effects cannot be exhibited.

Measures against low expression and lack of MHC molecules are very important objectives, considering the fact that even when CTL reactions caused by vaccines can be detected by immunological monitoring, they do not directly connect to antitumor effects. Furthermore, heterogeneity of tumors is also an important problem. Even when CTLs can be induced against one tumor antigen, in the case that expressed molecule is not an essential molecule for tumor growth, that molecule is deleted such that it is no longer a target of CTLs and the tumor can continue to grow. With the aim of solving the essential problems relating to antitumor effects of these vaccine therapies, the inventors focused their attention on VEGFR2 which is highly expressed in tumor neovascular endothelial cells and identified epitope peptides that can be used as vaccines [Wada S, Cancer Res. 65, 4939-4946, 2005., WO 2004/024766].

Conventionally, the combined use of vaccine therapy and chemotherapy has been considered incompatible based on their biological characteristics. However, from the standpoint of tumor immunity such as discovery of regulatory T cells and their cancellation, the possibility of a combined use with chemotherapy is being suggested. Therefore, clinical trials were planned to examine whether effects from the combined use of gemcitabine and peptide vaccine therapy targeting new tumor blood vessels can be expected for pancreatic cancer.

As a result, first, it was found to be fully acceptable in terms of safety. Regarding dose escalation, analyses of Grade 3 or higher systemic adverse events (at the completion of one course) showed that neutropenia and hepatic dysfunction appeared in one case out of three cases at level I, two cases out of three cases at level II, and one case out of two cases at level III; however, drug withdrawal or administration of G-CSF enabled continued administration. According to the above, at present, all levels are within the acceptable range. Since this is a vaccine therapy targeting tumor neovascular endothelial cells, bleeding tendency and other adverse events were of concern; however, the theoretical basis before carrying out the procedure, such as little expression in normal vascular endothelial cells, was proven to be correct to some degree. When dose escalation analyzed through immunological monitoring and clinical effects was analyzed in terms of DTH reaction, CTL reaction, and disease control rate, all were positive in two cases out of three cases at level I, and one case out of two cases in level III. At level II, CTL reaction alone was positive in three cases out of three cases (DTH reaction and the disease control rate were the same as in level I and III). While the number of cases is small, the above suggested the possibility that level II will be the recommended dose.

Regarding the antitumor effects, while the effect of combined use was clearly observed with vaccine chemotherapy, the possibility that the vaccine enhanced the antitumor effect of gemcitabine is discussed. As in the comparison of Table 8, the evident tumor reducing effect surpassed by two fold or more when compared to gemcitabine alone. This means that the direct antitumor effect of gemcitabine was enhanced by the vaccine. More specifically, it is conceivable that CTL induced by the vaccine destroyed the tumor neovascular endothelial cells such that gemcitabine was able to reach the tumor efficiently, and as a result, a strong antitumor effect was exhibited. Next, the possibility that gemcitabine enhanced the antitumor effects of the vaccine is discussed. Analysis of the immune response against the administered peptide confirmed that potent CTL reaction is induced mainly in clinically effective cases including SD cases. Furthermore, since the DTH reaction was enhanced, this strongly suggested the possibility that gemcitabine is enhancing the CTL reaction which is the core element of antitumor effects by the vaccine. Clinically as well, there were four out of five cases for which the antitumor effects has continued for a long period of time including SD (Case 4: one month; Case 6: two months; Case 7: two months, and Case 10: one month), and this is considered to be the result of long term antitumor effects by the vaccine. More specifically, this suggests the possibility that CTL is efficiently induced by gemcitabine, and this CTL leads to long term antitumor effects. Furthermore, there is the possibility that the tumor undergoes cell death due to gemcitabine, and this acts synergistically with the antitumor immune reactions activated by the vaccine. This way, enhancement of antitumor effects, including prolongation of the life span, without increasing side effects can be strongly expected through vaccine chemotherapy using gemcitabine and VEGFR2 peptides in combination. This can be considered to be great news towards the improvement of treatment outcome for pancreatic cancer with poor prognosis.

INDUSTRIAL APPLICABILITY

It was discovered herein that the therapeutic effect of chemotherapeutic agents against pancreatic cancer, for example, gemcitabine, can be significantly improved or enhanced when combined with an appropriate antigenic peptide, for example, the KDR peptide identified as a cancer vaccine in WO 2004/024766, the contents of which are incorporated by reference herein in their entirety. As such, the present invention provides an improved method for treating pancreatic cancer in a subject in need thereof.

All publications, databases, sequences, patents, and patent applications cited herein are hereby incorporated by reference.

While the invention has been described in detail and with reference to specific embodiments thereof, it will be apparent to one skilled in the art that various changes and modifications can be made therein without departing from the spirit and scope of the invention, the metes and bounds of which are set by the appended claims.

The invention claimed is:

1. A method of treating pancreatic cancer in a subject, comprising administering to said subject (i) and (ii);
   (i) one or more peptides selected from the group consisting of;
   (a) a peptide consisting of the amino acid sequence selected from the group consisting of RFVPDGNRI (SEQ ID NO: 1), VYSSEEAEL (SEQ ID NO: 2), GYRIYDVVL (SEQ ID NO: 3), SYMISYAGM (SEQ ID NO: 4), KWEFPRDRL (SEQ ID NO: 5), and DFLTLEHLI (SEQ ID NO: 6),
   (b) the peptide of (a), in which 1 or 2 amino acids are substituted, or added, and wherein said peptide has cytotoxic T cell inducibility;
   (c) the peptide of (b), wherein the second amino acid from the N-terminus is phenylalanine, tyrosine, methionine, or tryptophan; and
   (d) the peptide of (b) or (c), wherein the C-terminal amino acid is phenylalanine, leucine, isoleucine, tryptophan, or methionine
   (ii) one or more chemotherapeutic agents selected from the group consisting of gemcitabine, a pharmaceutically acceptable salt thereof, and a prodrug thereof.

2. The method of claim 1, wherein said subject is HLA-A24-positive.

3. A method of treating pancreatic cancer in a subject, comprising administering to said subject (i) and (ii);
   (i) one or more peptides selected from the group consisting of;
   (a) a peptide consisting of the amino acid sequence selected from the group consisting of AMFFWLLLV (SEQ ID NO: 7), VIAMFFWLL (SEQ ID NO: 8), AVIAMFFWL (SEQ ID NO: 9), KLIEIGVQT (SEQ ID NO: 10), YMISYAGMV (SEQ ID NO: 11), IQSDVWSFGV (SEQ ID NO: 12) and VLAMFFWLL (SEQ ID NO: 13);
   (b) the peptide of (a), in which 1 or 2 amino acids are substituted, or added, and wherein said peptide has cytotoxic T cell inducibility;
   (c) the peptide of (b), wherein the second amino acid from the N-terminus is leucine or methionine; and
   (d) the peptide of (b) or (c), wherein the C-terminal amino acid is valine or leucine;
   (ii) one or more chemotherapeutic agents selected from the group consisting of gemcitabine, a pharmaceutically acceptable salt thereof, and a prodrug thereof.

4. The method of claim 3, wherein said subject is HLA-A02-positive.

* * * * *

UNITED STATES PATENT AND TRADEMARK OFFICE
CERTIFICATE OF CORRECTION

| | | |
|---|---|---|
| PATENT NO. | : 8,703,713 B2 | Page 1 of 1 |
| APPLICATION NO. | : 12/674754 | |
| DATED | : April 22, 2014 | |
| INVENTOR(S) | : Yamaue et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 703 days.

Signed and Sealed this
Eleventh Day of August, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 9
<212> TYPE: PRT
<213> ORGANISM: Homo sapiens

<400> SEQUENCE: 1

Arg Phe Val Pro Asp Gly Asn Arg Ile
1               5

<210> SEQ ID NO 2
<211> LENGTH: 9
<212> TYPE: PRT
<213> ORGANISM: Homo sapiens

<400> SEQUENCE: 2

Val Tyr Ser Ser Glu Glu Ala Glu Leu
1               5

<210> SEQ ID NO 3
<211> LENGTH: 9
<212> TYPE: PRT
<213> ORGANISM: Homo sapiens

<400> SEQUENCE: 3

Gly Tyr Arg Ile Tyr Asp Val Val Leu
1               5
```

```
<210> SEQ ID NO 4
<211> LENGTH: 9
<212> TYPE: PRT
<213> ORGANISM: Homo sapiens

<400> SEQUENCE: 4

Ser Tyr Met Ile Ser Tyr Ala Gly Met
1               5

<210> SEQ ID NO 5
<211> LENGTH: 9
<212> TYPE: PRT
<213> ORGANISM: Homo sapiens

<400> SEQUENCE: 5

Lys Trp Glu Phe Pro Arg Asp Arg Leu
1               5

<210> SEQ ID NO 6
<211> LENGTH: 9
<212> TYPE: PRT
<213> ORGANISM: Homo sapiens

<400> SEQUENCE: 6

Asp Phe Leu Thr Leu Glu His Leu Ile
1               5

<210> SEQ ID NO 7
<211> LENGTH: 9
<212> TYPE: PRT
<213> ORGANISM: Homo sapiens

<400> SEQUENCE: 7

Ala Met Phe Phe Trp Leu Leu Leu Val
1               5

<210> SEQ ID NO 8
<211> LENGTH: 9
<212> TYPE: PRT
<213> ORGANISM: Homo sapiens

<400> SEQUENCE: 8

Val Ile Ala Met Phe Phe Trp Leu Leu
1               5

<210> SEQ ID NO 9
<211> LENGTH: 9
<212> TYPE: PRT
<213> ORGANISM: Homo sapiens

<400> SEQUENCE: 9

Ala Val Ile Ala Met Phe Phe Trp Leu
1               5

<210> SEQ ID NO 10
<211> LENGTH: 9
<212> TYPE: PRT
<213> ORGANISM: Homo sapiens

<400> SEQUENCE: 10

Lys Leu Ile Glu Ile Gly Val Gln Thr
1               5

<210> SEQ ID NO 11
<211> LENGTH: 9
```

```
<212> TYPE: PRT
<213> ORGANISM: Homo sapiens

<400> SEQUENCE: 11

Tyr Met Ile Ser Tyr Ala Gly Met Val
1               5

<210> SEQ ID NO 12
<211> LENGTH: 10
<212> TYPE: PRT
<213> ORGANISM: Artificial
<220> FEATURE:
<223> OTHER INFORMATION: Description of Artificial Sequence: Synthetic
      peptide

<400> SEQUENCE: 12

Ile Gln Ser Asp Val Trp Ser Phe Gly Val
1               5                   10

<210> SEQ ID NO 13
<211> LENGTH: 9
<212> TYPE: PRT
<213> ORGANISM: Artificial
<220> FEATURE:
<223> OTHER INFORMATION: Description of Artificial Sequence: Synthetic
      peptide

<400> SEQUENCE: 13

Val Leu Ala Met Phe Phe Trp Leu Leu
1               5
```